United States Patent [19]

Kikuchi et al.

[11] Patent Number: 5,684,003

[45] Date of Patent: Nov. 4, 1997

[54] 5-HT$_4$ RECEPTOR AGONISTS

[75] Inventors: Haruhiko Kikuchi; Hiroaki Satoh; Masashi Suzuki, all of Ohimachi; Ruta Fukutomi, Tokyo; Masahiro Ueno, Saitama-ken; Koichiro Hagihara; Takeo Arai, both of Ohimachi; Setsuko Mino; Yumiko Noguchi, both of Tokyo, all of Japan

[73] Assignee: Nisshin Flour Milling Co., Ltd., Tokyo, Japan

[21] Appl. No.: 543,853

[22] Filed: Oct. 12, 1995

[30] Foreign Application Priority Data

Oct. 20, 1994 [JP] Japan .................... 6-254907

[51] Int. Cl.$^6$ ................ A61K 31/535; C07D 413/12; C07D 498/08
[52] U.S. Cl. .................... 514/230.5; 544/105
[58] Field of Search .................... 544/105; 514/230.5

[56] References Cited

U.S. PATENT DOCUMENTS

| | | | |
|---|---|---|---|
| 5,187,166 | 2/1993 | Kikuchi et al. | 514/249 |
| 5,256,656 | 10/1993 | Kikuchi et al. | 514/224.2 |

FOREIGN PATENT DOCUMENTS

| | | |
|---|---|---|
| 0 377 967 | 7/1990 | European Pat. Off. . |
| 0 469 449 A1 | 2/1992 | European Pat. Off. . |
| 0 623 621 | 11/1994 | European Pat. Off. . |
| 2-202890 | 8/1990 | Japan . |
| WO 91/16045 | 10/1991 | WIPO . |

OTHER PUBLICATIONS

Trends in Pharmacological Science, vol. 13, "The 5-HT$_4$ Receptor: A Place in the Sun", Bockaert, et al. Apr. 1992, pp. 141-145.

J. Am. Chem. Soc., vol. 104, 6876-6877, (1982), Grochowski et al.

Naunyn-Schmiedeberg's Arch Pharmacol, "SDZ 205-557, A Selective, Surmountable Antagonist for 5-HT$_4$ Receptors in the Isolated Guinea Pig Ileum", Buchheit, et al. (1992) pp. 387-393.

Nauyn-Schmiedeberg's Arch Pharmacol, "5-Hydroxytryptamine$_4$, Receptors Mediate Relaxation of the Rat Oesophageal Tunica Muscularis Mucosae", Baxter, et al. (1991) pp. 439-446.

*Primary Examiner*—Philip I. Datlow
*Attorney, Agent, or Firm*—Oblon, Spivak, McClelland, Maier & Neustadt, P.C.

[57] ABSTRACT

Compounds of formula (I) and pharmaceutically acceptable salts thereof are selective agonists for 5-HT$_4$ receptors.

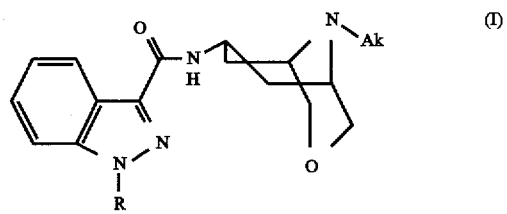

wherein Ak is a $C_3$–$C_6$ alkyl group, and R is a $C_2$–$C_6$ alkyl group, a $C_3$–$C_6$ alkenyl group, a $C_3$–$C_6$ alkynyl group, a $C_3$–$C_7$ cycloalkyl group or a $C_3$–$C_6$ cycloalkylmethyl group.

11 Claims, No Drawings

5-HT₄ RECEPTOR AGONISTS

FIELD OF THE INVENTION

This invention relates to new oxazabicyclo derivatives for use in the treatment of digestive tract diseases and 5-HT₄ receptor agonists comprising the same as an active ingredient.

BACKGROUND OF THE INVENTION

The abnormality in function of a gastrointestinal motility by various causes such as chronic gastritis, gastrectomy, peptic ulcer, diabetes mellitus or scleroderma results in the reflux of the gastric contents into the esophagus, delayed emptying of the contents and the depression of the small and large intestinal function. This can lead to several gastrointestinal disorders including nausea, vomiting, heartburn, anorexia, abdominal distension, epigastric dysphoria, abdominaglia, constipation and further reflux esophagitis. One cause of the diseases such as irritable bowel syndrome and spurious ileus is considered to be the depression in gastrointestinal motility.

The agents for the treatment of these conditions and diseases include direct cholinergic agent Aclatonium Napadisilate) or Dopamine antagonist (e.g. Domperidone). However, it is reported that these known agents have the problems of insufficient therapeutic effects and side effects including diarrhea and extrapyramidal syndrome.

The gastrointestinal motility is controlled by sympathetic and parasympathetic nerves. In parasympathetic nerve, acetylcholine is one of the most important neurotransmitters participating in the control of gastrointestinal motility. The release of acetylcholine from the nerve in the nerve plexus of the gastrointestinal tract may induce the contraction of gastrointestinal tract. Accordingly, the accelerated release of acetylcholine from the nerve plexus of gastrointestinal tract results in sthenia of gastrointestinal motility.

Recently, it was reported that a 5-HT₄ receptor is found in gastrointestinal tract. The 5-HT₄ receptor was reported to control the release of acetylcholine in gastrointestinal nerve [Trends in Pharmacological Science, Vol. 13, 141–145, (1992)]. Thus, compounds acting on the 5-HT₄ receptor in gastrointestinal tract and promoting the release of acetylcholine may be a more effective gastrokinetic agent with less side-effects. On the other hand, Japanese Patent Kokai 2-202890 and EPA 469449 disclose that N-[endo-9-methyl-3-oxa-9-azabicyclo[3.3.1]non-7-yl]indazole-3-carboxamide derivatives have an antagonism at 5-HT₃ receptors. However, it is not reported that they have an agonism at 5-HT₄ receptors.

DETAILED DESCRIPTION OF THE INVENTION

The present inventors have found that certain class of oxazabicyclo derivatives and their metabolites have a strong 5-HT₄ receptor agonistic activity but have no or little 5-HT₃ receptor antagonistic activity, i.e. having a potent and selective 5-HT₄ receptor agonistic activity and exhibiting a gastrointestinal prokinetic action, by which they are effective for the treatment of digestive tract diseases.

The present invention provides a compound of formula (I)

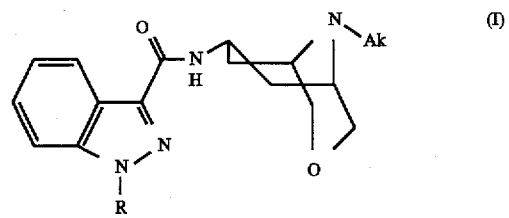

wherein Ak is a $C_3$–$C_6$ alkyl group and R is a $C_2$–$C_6$ alkyl group, a $C_3$–$C_6$ alkenyl group, a $C_3$–$C_6$ alkynyl group, a $C_3$–$C_7$ cycloalkyl group or a $C_3$–$C_6$ cycloalkylmethyl group, pharmaceutically acceptable salts and metabolites thereof.

Examples of the $C_3$–$C_6$ alkyl group for Ak include n-propyl, isopropyl, n-butyl, isobutyl, sec-butyl, tert-butyl, n-pentyl, isopentyl, 2-pentyl, 3-pentyl, neo-pentyl, tert-pentyl and hexyl. Examples of the $C_2$–$C_6$ alkyl group for R include ethyl, n-propyl, isopropyl, n-butyl, isobutyl, sec-butyl, (S)-sec-butyl, (R)-sec-butyl, tert-butyl, n-pentyl, isopentyl, 2-pentyl, 3-pentyl, neo-pentyl, tert-pentyl and hexyl. The $C_3$–$C_6$ alkenyl group includes allyl, 2-butenyl, 3-butenyl, 2-methyl-2-propenyl, 1-methyl-2-propenyl and 3-methyl-2-butenyl. The $C_3$–$C_6$ alkynyl group includes 1-propynyl, 2-propynyl, 2-butynyl and 1-methyl-2-butynyl. The $C_3$–$C_7$ cycloalkyl group includes cyclopropyl, cyclobutyl, cyclopentyl, cyclohexyl and cycloheptyl. The $C_3$–$C_6$ cycloalkylmethyl group includes cyclopropylmethyl, cyclobutylmethyl, cyclopentylmethyl and cyclohexylmethyl.

The compounds of formula (I) may be prepared, for instance, by reacting a 7-amino-9-alkyl-3-oxa-9-azabicyclo[3.3.1]nonane derivative with a compound of formula (II)

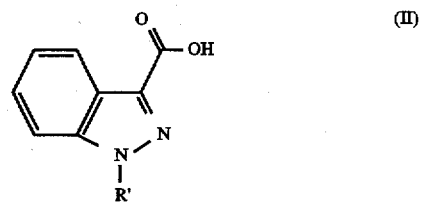

wherein R' is a hydrogen atom or has the same meaning as defined for R or a reactive derivative thereof (e.g. acid halides, mixed acid anhydrides with lower fatty acids, mixed acid anhydrides with halogenated lower fatty acids, etc) or with a compound of formula (III)

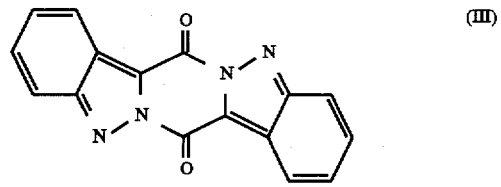

Alternatively, the resulting compounds wherein R' is hydrogen may be reacted, for instance, with a compound of formula (IV), RX wherein R has the same meaning as defined above and X is halogen or OH to produce the compounds of formula (I).

For example, 7-amino-9-alkyl-3-oxa-9-azabicyclo[3.3.1] nonane derivatives are reacted with a compound of formula (III) to afford the carboxamide form which is then reacted with a compound of formula (IV) to prepare a compound of formula (I) wherein R is as defined above. This reaction is shown in Reaction Scheme 1.

Reaction Scheme 1

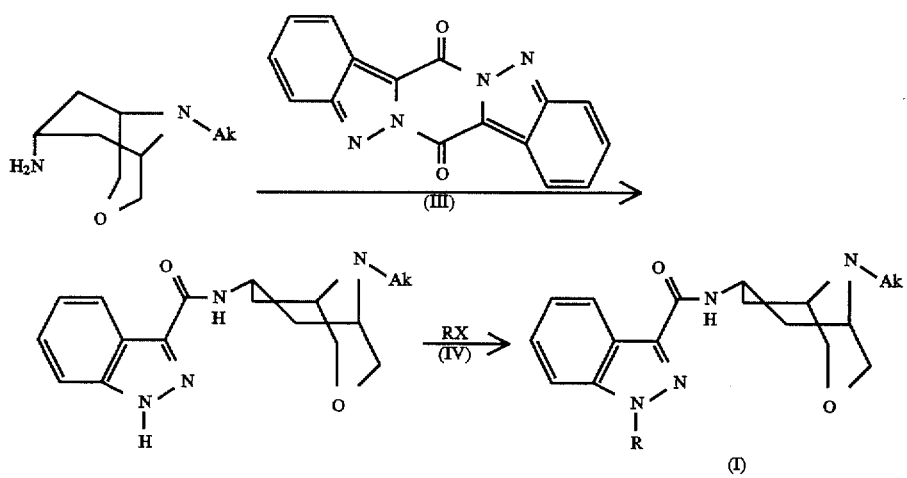

The 7-amino-9-alkyl-3S-oxa-9-azabicyclo[3.3.1]nonane derivatives may be prepared, for example, by oxidizing 2,5-dihydrofuran or 3,4-dihydroxytetrahydrofuran to 3-oxa-1,5-pentanedial which is then reacted with an alkylamine and acetonedicarboxylic acid (or an acetonedicarboxylic acid diester derivative) to form a 9-alkyl-3-oxa-9-azabicyclo [3.3.1]nonan-7-one derivative, converting the carbonyl group on the oxazabicyclo ring to the corresponding oxime, followed by reduction of the oxime, or alternatively reacting the 9-alkyl-3-oxa-9-azabicyclo[3.3.1]nonan-7-one derivative with ammonia, converting the carbonyl group to the corresponding imino group and reducing the imino compound. This reaction is shown in Reaction Scheme 2.

2,5-dihydrofuran at a temperature of −100° C. to room temperature, preferably −78° C. to 0° C. The solvents which may be employed in this reaction may include hydrocarbons such as pentane, hexane, heptane, cyclohexane, petroleum ether or benzene; halogenated hydrocarbons such as carbon tetrachloride, chloroform or methylene chloride; ethers such as ethyl ether, THF or dioxane; esters such as ethyl acetate; acetone; DMF; nitromethane; acetic anhydride; carboxylic acids such as formic acid or acetic acid; alcohols such as methanol, ethanol or propanol, and water. Methanol is preferred.

Following ozone oxidation, dimethyl sulfide is added dropwise to a reaction vessel. Dimethyl sulfide is employed

Reaction Scheme 2

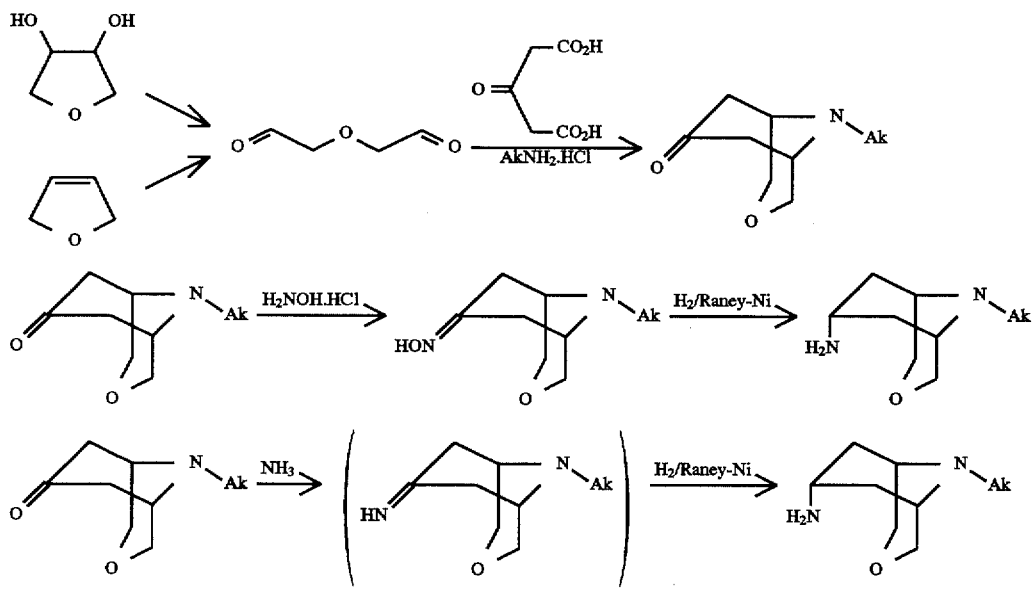

The reaction conditions used in the present processes will be discussed in detail.

In preparing 3-oxa-1,5-pentanedial, ozone oxidation is carried out using a slight excess—10 molar amount, preferably 1.001–2 molar amount, of ozone gas per mole of in a molar amount of 1–10 moles, preferably 1–4 moles, per mole of 2,5-dihydrofuran and it is added dropwise at a temperature from −100° C. to a boiling point of the solvent employed, preferably −78° C. After the temperature is allowed to be raised up to room temperature, the reaction is carried out. The 3-oxa-1,5-pentanedial thus obtained may be added dropwise to the reaction solution for subsequent Robinson-Schöpf Reaction without any purification.

Alternatively, 3,4-dihydroxytetrahydrofuran may be reacted with a 0.1–10 molar amount of periodic acid or a periodate at a temperature of −78° C. to room temperature.

Illustrative examples of the periodates include sodium periodate and potasssium periodate.

The solvents which may be employed may include ethers such as ethyl ether, isopropyl ether, THF or dioxane; alcohols such as methanol, ethanol, or propanol; and water. Water, methanol and isopropyl ether are preferably employed.

The resulting 3-oxa-1,5-pentanedial may be added dropwise to the reaction solution for subsequent Robinson-Schöpf Reaction without any purification.

The 9-alkyl-3-oxa-9-azabicyclo[3.3.1]nonan-7-one derivative may be obtained by Robinson-Schöpf Reaction of the 3-oxa-1,5-pentanedial synthesized as described above with an alkylamine derivative and acetone dicarboxylic acid (or an acetonedicarboxylic acid diester derivative).

Illustrative examples of the alkylamine derivatives may include n-propylamine, isopropylamine, n-butylamine, isobutylamine, sec-butylamine, tert-butylamine, n-pentylamine, isopentylamine, 2-pentylamine, 3-pentylamine, neo-pentylamine, tert-pentylamine and hexylamine.

Illustartive examples of the acetonedicarboxylic acid diester derivatives may include dimethyl acetonedicarboxylate, diethyl acetonedicarboxylate, dipropyl acetonedicarboxylate and diisopropyl acetonedicarboxylate.

Robinson-Schöpf Reaction may be carried out using a 0.5–10 molar, preferably 1–3 molar, amount of the alkylamine, a 0.5–10 molar, preferably 1–3 molar, amount of the acetonedicarboxylic acid per mole of the 2,5-dihydrofuran. The reaction may be carried out at a temperature from a freezing point to a boiling point of the solvent employed, preferably a temperature of 0° C.–40° C.

In the case where the acetonedicarboxylic acid ester is employed, a base or acid is added after the Robinson-Schöpf Reaction and the reaction is further carried out.

The solvents which may be employed may include alcohols such as methanol, ethanol and propanol; and water. For a pH control, there may be added carboxylic acids such as formic acid, acetic acid and citric acid; salts such as disodium hydrogenphosphate and sodium hydrogenphosphate; inorganic acids such as hydrochloric acid, sulfuric acid, phosphoric acid and nitric acid; or bases such as sodium hydroxide or potassium hydroxide, triethylamine and pyridine. The alkylamine derivative may be added in the form of its salt such as hydrochloride and the like.

The 9-alkyl-3-oxa-9-azabicyclo[3.3.2]nonan-7-one oxime derivatives (oxime form) may be prepared by reacting the 9-alkyl-3-oxa-9-azabicyclo[3.3.1]nonan-7-one derivatives with hydroxylamine hydrochloride in the presence of a base.

Illustrative examples of the 9-alkyl-3-oxa-9-azabicyclo [3.3.1]nonan-7-one derivatives may include:
9-(n-Propyl)-3-oxa-9-azabicyclo[3.3.1]nonan-7-one,
9-isopropyl-3-oxa-9-azabicyclo[3.3.1]nonan-7-one,
9-(n-butyl)-3-oxa-9-azabicyclo[3.3.1]nonan-7-one,
9-isobutyl-3-oxa-9-azabicyclo[3.3.1]nonan-7-one,
9-(sec-butyl)-3-oxa-9-azabicyclo[3.3.1]nonan-7-one,
9-(tert-butyl)-3-oxa-9-azabicyclo[3.3.1]nonan-7-one,
9-(n-pentyl)-3-oxa-9-azabicyclo[3.3.1]nonan-7-one,
9-isopentyl-3-oxa-9-azabicyclo[3.3.1]nonan-7-one,
9-(2-pentyl)-3-oxa-9-azabicyclo[3.3.1]nonan-7-one,
9-(3-pentyl)-3-oxa-9-azabicyclo[3.3.1]nonan-7-one,
9-(neo-pentyl)-3-oxa-9-azabicyclo[3.3.1]nonan-7-one,
9-(tert-pentyl)-3-oxa-9-azabicyclo[3.3.1]nonan-7-one, and
9-hexyl-3-oxa-9-azabicyclo[3.3.1]nonan-7-one.

Illustrative examples of the bases may include pyridine, 4-dimethylaminopyridine, triethylamine and 1,8-diazabicyclo[5.4.0]-7-undecene.

This reaction is carried out using a 0.5–10 molar, preferably 0.9–2 molar, amount of hydroxylamine hydrochloride and a 0.5–10 molar, preferably 0.9–3 molar, amount of the base per mole of the 9-alkyl-3-oxa-9-azabicyclo[3.3.1] nonan-7-one derivative. The reaction may be carried out at a temperature of 0° C. to a boiling point of the solvent employed, preferably room temperature to a boiling point of the solvent. The solvents which may be employed may include alcohols such as methanol, ethenol and propanol.

The endo-7-amino-9-alkyl-3-oxa-9-azabicyclo[3.3.1] nonane derivatives may be prepared by reducing the oxime derivatives in the presence of Raney nickel catalyst under hydrogen atmosphere.

Illustrative examples of the oxime derivatives which may be employed include:
9-(n-Propyl)-3-oxa-9-azabicyclo[3.3.1]nonan-7-one oxime,
9-isopropyl-3-oxa-9-azabicyclo[3.3.1]nonan-7-one oxime,
9-(n-butyl)-3-oxa-9-azabicyclo[3.3.1]nonan-7-one oxime,
9-isobutyl-3-oxa-9-azabicyclo[3.3.1]nonan-7-one oxime, Illustrative examples of the 9-alkyl-3-oxa-9-azabicyclo [3.3.1]nonan-7-one derivatives may include:
9-(n-Propyl)-3-oxa-9-azabicyclo[3.3.1]nonan-7-one,
9-isopropyl-3-oxa-9-azabicyclo[3.3.1]nonan-7-one,
9-(n-butyl)-3-oxa-9-azabicyclo[3.3.1]nonan-7-one,
9-isobutyl-3-oxa-9-azabicyclo[3.3.1]nonan-7-one,
9-(sec-butyl)-3-oxa-9-azabicyclo[3.3.1]nonan-7-one,
9-(tert-butyl)-3-oxa-9-azabicyclo[3.3.1]nonan-7-one,
9-(n-pentyl)-3-oxa-9-azabicyclo[3.3.1]nonan-7-one,
9-isopentyl-3-oxa-9-azabicyclo[3.3.1]nonan-7-one,
9-(2-pentyl)-3-oxa-9-azabicyclo[3.3.1]nonan-7-one,
9-(3-pentyl)-3-oxa-9-azabicyclo[3.3.1]nonan-7-one,
9-(neo-pentyl)-3-oxa-9-azabicyclo[3.3.1]nonan-7-one,
9-(tert-pentyl)-3-oxa-9-azabicyclo[3.3.1]nonan-7-one, and
9-hexyl-3-oxa-9-azabicyclo[3.3.1]nonan-7-one.

The imination and reduction reaction is carried out using a not less than equivalent amount of aqueous ammonia, gaseous ammonia or liquid ammonia or an amount thereof to be employed as a solvent and a 0.01–10 times, preferably 0.02–2 times, amount of Raney nickel based on the weight of the nonane derivatives at a hydrogen pressure of ordinary pressure −150 kg/cm$^2$, preferably 10–100 kg/cm$^2$ and a reaction temperature of −78° to 200° C., preferably room temperature to 100° C. The solvents which may be employed may include water (aqueous ammonia), liquid ammonia, alcohols such as methanol, ethanol and propanol.
9-(sec-butyl)-3-oxa-9-azabicyclo[3.3.1]nonan-7-one oxime,
9-(tert-butyl)-3-oxa-9-azabicyclo[3.3.1]nonan-7-one oxime,
9-(n-pentyl)-3-oxa-9-azabicyclo[3.3.1]nonan-7-one oxime,
9-isopentyl-3-oxa-9-azabicyclo[3.3.1]nonan-7-one oxime,
9-(2-pentyl)-3-oxa-9-azabicyclo[3.3.1]nonan-7-one oxime,
9-(3-pentyl)-3-oxa-9-azabicyclo[3.3.1]nonan-7-one oxime,
9-(neo-pentyl)-3-oxa-9-azabicyclo[3.3.1]nonan-7-one oxime,
9-(tert-pentyl)-3-oxa-9-azabicyclo[3.3.1]nonan-7-one oxime, and
9-hexyl-3-oxa-9-azabicyclo[3.3.1]nonan-7-one oxime.

The reduction of the oxime form is carried out using a 2–50 molar, preferably 5–20 molar, amount of ammonium acetate per mole of the oxime and a 0.01–10 times, preferably 0.02–2 times, amount of Raney nickel based on the weight of the oxime, at a hydrogen pressure of ordinary pressure −150 kg/cm², preferably 10–100 kg/cm² and a reaction temperature of room temperature −200° C., preferably room temperature −100° C. The solvents which may be employed may include alcohols such as methanol, ethanol and propanol.

Alternatively, the endo-7-amino-9-alkyl-3-oxa-9-azabicyclo[3.3.1]nonane derivatives may be prepared by imination and subsequent reduction of the 9-alkyl-3-oxa-9-azabicyclo[3.3.1]nonan-7-one derivatives in the presence of ammonia and Raney nickel catalyst under hydrogen atmosphere.

The compounds of formula (I) can be prepared by reacting the endo-7-amino-9-alkyl-3-oxa-9-azabicyclo[3.3.1]nonane derivatives with reactive derivatives of various carboxylic acids or with a carboxylic acid in the presence of a condensation agent such as carbodiimide derivatives and diethyl phosphorocyanidates.

Illustrative examples of the endo-7-amino-9-alkyl-3-oxa-9-azabicyclo[3.3.1]nonane derivatives may include:
endo-7-amino-9-(n-propyl)-3-oxa-9-azabicyclo[3.3.1]nonane,
endo-7-amino-9-isopropyl-3-oxa-9-azabicyclo[3.3.1]nonane,
endo-7-amino-9-(n-butyl)-3-oxa-9-azabicyclo[3.3.1]nonane,
endo-7-amino-9-isobutyl-3-oxa-9-azabicyclo[3.3.1]nonane,
endo-7-amino-9-(sec-butyl)-3-oxa-9-azabicyclo[3.3.1]nonane,
endo-7-amino-9-(tert-butyl)-3-oxa-9-azabicyclo[3.3.1]nonane,
endo-7-amino-9-(n-pentyl)-3-oxa-9-azabicyclo[3.3.1]nonane,
endo-7-amino9-isopentyl-3-oxa-9-azabicyclo[3.3.1]nonane,
endo-7-amino-9-(2-pentyl)-3-oxa-9-azabicyclo[3.3.1]nonane,
endo-7-amino-9-(3-pentyl)-3-oxa-9-azabicyclo[3.3.1]nonane,
endo-7-amino-9-(neo-pentyl)-3-oxa-9-azabicyclo[3.3.1]nonane,
endo-7-amino-9-(tert-pentyl)-3-oxa-9-azabicyclo[3.3.1]-nonane, and
endo-7-amino-9-hexyl-3-oxa-9-azabicyclo[3.3.1]nonane.

Illustrative examples of the carboxylic acid reactive derivatives may include:
diindazolo[2,3-a][2',3'-d]pyrazine-7,14-dione,
1-ethylindazole-3-carbonyl chloride,
1-(n-propyl)indazole-3-carbonyl chloride,
1-isopropylindazole-3-carbonyl chloride,
1-(n-butyl)indazole-3-carbonyl chloride,
1-isobutylindazole-3-carbonyl chloride,
1-(sec-butyl)indazole-3-carbonyl chloride,
(S)-1-(sec-butyl)indazole-3-carbonyl chloride,
(R)-1-(sec-butyl)indazole-3-carbonyl chloride,
1-(n-pentyl)indazole-3-carbonyl chloride,
1-(isopentyl)indazole-3-carbonyl chloride,
1-(2-pentyl)indazole-3-carbonyl chloride,
1-(3-pentyl)indazole-3-carbonyl chloride,
1-(neo-pentyl)indazole-3-carbonyl chloride,
1-allylindazole-3-carbonyl chloride,
1-(2-butenyl)indazole-3-carbonyl chloride,
1-(3-butenyl)indazole-3-carbonyl chloride,
1-(2-methyl-2-propenyl)indazole-3-carbonyl chloride,
1-(1-methyl-2-propenyl)indazole-3-carbonyl chloride,
1-(3-methyl-2-butenyl)indazole-3-carbonyl chloride,
1-(1-propynyl)indazole-3-carbonyl chloride,
1-(2-propynyl)indazole-3-carbonyl chloride,
1-(2-butynyl)indazole-3-carbonyl chloride,
1-(1-methyl-2-butynyl)indazole-3-carbonyl chloride,
1-cyclobutylindazole-3-carbonyl chloride,
1-cyclopentylindazole-3-carbonyl chloride,
1-cyclohexylindazole-3-carbonyl chloride, and
1-(cyclopropylmethyl)indazole-3-carbonyl chloride.

In the reaction of the endo-7-amino-9-alkyl-3-oxa-9-azabicyclo[3.3.1]nonane derivative with the reactive derivatives of carboxylic acid, the reaction is carried out using a 0.1–10 molar, preferably 0.25–2 molar, amount of the reactive derivatives per mole of the endo-7-amino-9-alkyl-3-oxa-9-azabicyclo[3.3.1]nonane. The reaction is carried out at a temperature between a freezing point and a boiling point of the solvent employed, preferably at a temperature of 0–4° C. The solvents which may be employed include hydrocarbons such as pentane, hexane, heptane, cyclohexane, petroleum ether and benzene; halogenated hydrocarbons such as carbon tetrachloride, chloroform and methylene chloride; ethers such as ethyl ether, THF and dioxane; esters such as ethyl acetate; acetone, DMF, nitromethane; DMSO; HMPA and pyridine, DMF and DMSO being preferred. In this reaction, bases may be used, if necessary, such as dimethylaminopyridine, triethylamine, pyridine, potassium carbonate and sodium carbonate.

Illustrative examples of the carboxylic acids which may be employed may include:
1-ethylindazole-3-carboxylic acid,
1-(n-propyl)indazole-3-carboxylic acid,
1-isopropylindazole-3-carboxylic acid,
1-(n-butyl)indazole-3-carboxylic acid,
1-isobutylindazole-3-carboxylic acid,
1-(sec-butyl)indazole-3-carboxylic acid,
(S)-1-(sec-butyl)indazole-3-carboxylic acid,
(R)-1-(sec-butyl)indazole-3-carboxylic acid,
1-(n-pentyl)indazole-3-carboxylic acid,
1-(isopentyl)indazole-3-carboxylic acid,
1-(2-pentyl)indazole-3-carboxylic acid,
1-(3-pentyl)indazole-3-carboxylic acid,
1-(neo-pentyl)indazole-3-carboxylic acid,
1-allylindazole-3-carboxylic acid,
1-(2-butenyl)indazole-3-carboxylic acid,
1-(3-butenyl)indazole-3-carboxylic acid,
1-(2-methyl-2-propenyl)indazole-3-carboxylic acid,
1-(1-methyl-2-propenyl)indazole-3-carboxylic acid,
1-(3-methyl-2-butenyl)indazole-3-carboxylic acid,
1-propynylindazole-3-carboxylic acid,
1-(2-propynyl)indazole-3-carboxylic acid,
1-(2-butynyl)indazole-3-carboxylic acid,
1-(1-methyl-2-butynyl)indazole-3-carboxylic acid,
1-cyclobutylindazole-3-carboxylic acid,
1-cyclopentylindazole-3-carboxylic acid,
1-cyclohexylindazole-3-carboxylic acid,
1-(cyclopropylmethyl)indazole-3-carboxylic acid, and
1H-indazole-3-carboxylic acid.

Illustrative examples of the carbodiimide derivatives may include dicyclohexylcarbodiimide and 1-ethyl-3-(3'-dimethylaminopropyl)carbodiimide hydrochloride.

Condensation of the endo-7-amino-9-alkyl-3-oxa-9-azabicyclo[3.3.1]nonane derivative with the carboxylic acid is carried out using a 0.1–10 molar, preferably 0.5–2 molar, amount of the carboxylic acid and a 0.1–10 molar, preferably 0.5–2 molar, amount of the carbodiimide derivative per mole of the endo-7-amino-9-alkyl-3-oxa-9-azabicyclo[3.3.1]nonane derivative. In this reaction, a 0.5–2 molar amount of 1-hydroxybenzotriazole or N-hydroxysuccinimide may be used, if necessary. The reaction may be carried out at a temperature between a freezing point and a boiling point of the solvent employed, preferably 0°–40° C. The solvents which may be employed may include hydrocarbons such as pentane, hexane, heptane, cyclohexane, petroleum ether and benzene; halogenated hydrocarbons such as carbon tetrachloride, chloroform and methylene chloride; ethers such as ethyl ether, THF and dioxane; esters such as ethyl acetate; acetone; DMF, nitromethane and DMSO, DMF and methylene chloride being preferred.

The compounds of formula (I) can be prepared by reacting the N-[endo-9-alkyl-3-oxa-9-azabicyclo-[3.3.1]non-7-yl]-1H-indazole-3-carboxamide derivatives with a compound of formula (IV), RX wherein X is halogen in the presence of a base.

Illustrative examples of the N-[endo-9-alkyl-3-oxa-9-azabicyclo[3.3.1]non-7-yl]-1H-indazole-3-carboxamide derivatives may include:

N-[endo-9-(n-Propyl)-3-oxa-9-azabicyclo[3.3.1]non-7-yl]-1H-indazole-carboxamide,
N-[endo-9-isopropyl-3-oxa-9-azabicyclo[3.3.1]non-7-yl]-1H-indazole-carboxamide,
N-[endo-9-(n-butyl)-3-oxa-9-azabicyclo[3.3.1]non-7-yl]-1H-indazole-carboxamide,
N-[endo-9-isobutyl-3-oxa-9-azabicyclo[3.3.1]non-7-yl]-1H-indazole-carboxamide,
N-[endo-9-(sec-butyl)-3-oxa-9-azabicyclo[3.3.1]non-7-yl]-1H-indazole-carboxamide,
N-[endo-9-(tert-butyl)-3-oxa-9-azabicyclo[3.3.1]non-7-yl]-1H-indazole-carboxamide,
N-[endo-9-(n-pentyl)-3-oxa-9-azabicyclo[3.3.1]non-7-yl]-1H-indazole-carboxamide,
N-[endo-9-isopentyl-3-oxa-9-azabicyclo[3.3.1]non-7-yl]-1H-indazole-carboxamide,
N-[endo-9-(2-pentyl)-3-oxa-9-azabicyclo[3.3.1]non-7-yl]-1H-indazole-carboxamide,
N-[endo-9-(3-pentyl)-3-oxa-9-azabicyclo[3.3.1]non-7-yl]-1H-indazole-carboxamide,
N-[endo-9-(neo-pentyl)-3-oxa-9-azabicyclo[3.3.1]non-7-yl]-1H-indazole-carboxamide,
N-[endo-9-(tert-pentyl)-3-oxa-9-azabicyclo[3.3.1]non-7-yl]-1H-indazole-carboxamide, and
N-[endo-9-hexyl-3-oxa-9-azabicyclo[3.3.1]non-7-yl]-1H-indazole-carboxamide.

Illustrative examples of the compounds RX may include ethyl bromide, ethyl iodide, n-propyl bromide, isopropyl chloride, isopropyl bromide, isopropyl iodide, n-butyl bromide, isobutyl chloride, isobutyl bromide, isobutyl iodide, sec-butyl chloride, sec-butyl bromide, sec-butyl iodide, (S)-sec-butyl chloride, (S)-sec-butyl bromide, (S)-sec-butyl iodide, n-pentyl bromide, isopentyl bromide, 2-pentyl bromide, 3-pentyl bromide, neo-pentyl bromide, allyl bromide, 2-butenyl bromide, 3-butenyl bromide, 2-methyl-2-propenyl bromide, 1-methyl-2-propenyl bromide, 3-methyl-2-butenyl bromide, propargyl bromide, 2-butynyl bromide, 1-methyl-2-butynyl bromide, bromocyclopropane, bromocyclobutane, bromocyclopentane, bromocyclohexane and bromomethylcyclopropane.

Illustrative examples of the bases which may be employed may include sodium hydride and n-butyl lithium. The reaction of the N-[endo-9-alkyl-3-oxa-9-azabicyclo-[3.3.1]non-7-yl]-1H-indazole-3-carboxamide derivative with the compound RX is carried out using a 0.1–10 molar, preferably 0.8–1.2 molar, amount of the base and a 0.1–10 molar, preferably 0.5–3 molar, amount of the compound RX per mole of the N-[endo-9-alkyl-3-oxa-9-azabicyclo-[3.3.1]non-7-yl]-1H-indazole-3-carboxamide derivative. The reaction is carried out at a temperature of from a freezing point to a boiling point of the solvent employed, preferably at 0°–40° C. The solvent which may be employd may include hydrocarbons such as pentane, hexane, heptane, cyclohexane, petroleum ether and benzene; ethers such as ethyl ether, THF and dioxane; esters such as ethyl acetate; DMF; and DMSO, DMF being preferred.

Alternatively, the compounds of formula (I) may be prepared by reacting the N-[endo-9-alkyl-3-oxa-9-azabicyclo[3.3.1]non-7-yl]-1H-indazole-3-carboxamide derivative with a compound of formula (IV), RX wherein X is OH [J. Am. Chem. Soc., Vol. 104, 6876, (1982)].

Illustartive examples of the ROH compounds may include sec-butyl alcohol, (R)-(−)-sec-butyl alcohol, (S)-(+)-sec-butyl alcohol, propargyl alcohol, 2-butynyl alcohol, 1-methyl-2-butynyl alcohol, cyclopropyl alcohol, cyclobutyl alcohol, cyclopentyl alcohol, and cyclohexyl alcohol.

The reaction is carried out using a 0.5–2 molar, preferably 0.8–1.2 molar, amount of diethylazodicarboxylate (or diisopropylazodicarboxylate), a 0.5–2 molar, preferably 0.8–1.2 molar, amount of triphenylphosphine (or tributylphosphine) and a 0.5–2 molar, preferably 0.8–1.2 molar, amount of the ROH compound per mole of the N-[endo-9-alkyl-3-oxa-9-azabicyclo[3.3.1]non-7-yl]-1H-indazole-3-carboxamide derivative. The reaction is carried out at a temperature between a freezing point and a boiling point of the solvent employed, preferably at a temperature of 0°–100° C. For the solvents, ethers (e.g., ethyl ether, THF, dioxane) and DMF are preferably used.

Illustrative examples of the present compounds thus produced may include:
N-[endo-9-(n-Propyl)-3-oxa-9-azabicyclo[3.3.1]non-7-yl]-1-isopropylindazole-3-carboxamide,
N-[endo-9-(n-propyl)-3-oxa-9-azabicyclo[3.3.1]non-7-yl]-1-(3-pentyl)indazole-3-carboxamide,
N-[endo-9-(n-butyl)-3-oxa-9-azabicyclo[3.3.1]non-7-yl]-1-ethylindazole-3-carboxamide,
N-[endo-9-(n-butyl)-3-oxa-9-azabicyclo[3.3.1]non-7-yl]-1-(n-propyl)indazole-3-carboxamide,
N-[endo-9-(n-butyl)-3-oxa-9-azabicyclo[3.3.1]non-7-yl]-1-isopropylindazole-3-carboxamide
N-[endo-9-(n-butyl)-3-oxa-9-azabicyclo[3.3.1]non-7-yl]-1-(n-butyl)indazole-3-carboxamide
N-[endo-9-(n-butyl)-3-oxa-9-azabicyclo[3.3.1]non-7-yl]-1-isobutylindazole-3-carboxamide
N-[endo-9-(n-butyl)-3-oxa-9-azabicyclo[3.3.1]non-7-yl]-1-(sec-butyl)indazole-3-carboxamide
(S)-(+)-N-[endo-9-(n-butyl)-3-oxa-9-azabicyclo[3.3.1]non-7-yl]-1-(sec-butyl)indazole-3-carboxamide
(R)-(−)-N-[endo-9-(n-butyl)-3-oxa-9-azabicyclo[3.3.1]non-7-yl]-1-(sec-butyl)indazole-3-carboxamide
N-[endo-9-(n-butyl)-3-oxa-9-azabicyclo[3.3.1]non-7-yl]-1-(2-pentyl)indazole-3-carboxamide
N-[endo-9-(n-butyl)-3-oxa-9-azabicyclo[3.3.1]non-7-yl]-1-(3-pentyl)indazole-3-carboxamide
N-[endo-9-(n-butyl)-3-oxa-9-azabicyclo[3.3.1]non-7-yl]-1-allylindazole-3-carboxamide
N-[endo-9-(n-butyl)-3-oxa-9-azabicyclo[3.3.1]non-7-yl]-1-(3-methyl-2-butenyl)indazole-3-carboxamide
N-[endo-9-(n-butyl)-3-oxa-9-azabicyclo[3.3.1]non-7-yl]-1-(1-methyl-2-butynyl)indazole-3-carboxamide
N-[endo-9-(n-butyl)-3-oxa-9-azabicyclo[3.3.1]non-7-yl]-1-(cyclopropylmethyl)indazole-3-carboxamide
N-[endo-9-(n-butyl)-3-oxa-9-azabicyclo[3.3.1]non-7-yl]-1-cyclopentyl-indazole-3-carboxamide
N-[endo-9-(n-pentyl)-3-oxa-9-azabicyclo[3.3.1]non-7-yl]-1-isopropylindazole-3-carboxamide N-[endo-9-(n-pentyl)-3-oxa-9-azabicyclo[3.3.1]non-7-yl]-1-(3-pentyl)indazole-3-carboxamide.

The above compounds of the present invention exhibit a 5-HT$_4$ receptor agonistic activity as demonstrated in Examples 29 and 30 which will be given later, but exhibit less 5-HT$_3$ receptor antagonistic activity as shown in Example 31. Thus the present compounds are selective agonists for 5-HT$_4$ receptors. Further, the compounds of the present invention possess potent gastrointestinal prokinetic action via 5-HT$_4$ receptors as demonstrated in Examples 32 and 33, which are useful as a therapeutic agent for digestive tract diseases, such as gastrointestinal prokinetic agent. Illustrative examples of digestive tract diseases include gastrointestinal symptom (nausea, vomiting, pyrosis, anorexia, abdominal distention, epigastric dysphoria, abdominal pain, constipation, etc.) due to chronic gastritis, postgastrectomy syndrome, peptic ulcer, diabetes, scleroderma and others; regurgitant esophagitis; irritable bowel syndrome; and spurious ileus.

Some of the compounds of formula (I), metabolizing in the living body, can be converted to 5-HT$_4$ receptor agonist which is useful in the treatment of digestive tract diseases. A principal metabolizable moiety is indicated below with arrows (1)–(4) in formula (I).

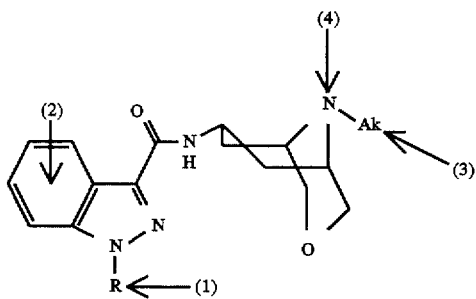

Note:
(1) Removal or hydroxylation of the substituent R at the 1-position of the indazole ring
(2) Hydroxylation at the 4-, 5-, 6- and 7- positions of the indazole ring
(3) Removal or hydroxylation of the substituent Ak at the 9-position of the oxazabicyclo ring
(4) N-oxide formation of the nitrogen atom at the 9-position of the oxazabicyclo ring
(5) Conjugates of the above metabolites with glucuronic acid, sulfuric acid or glutathione The metabolites are represented by formula (V)

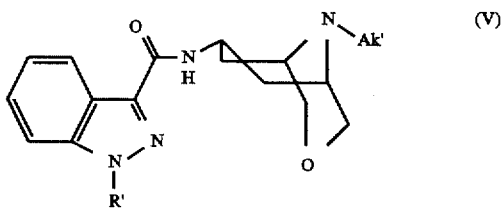

wherein Ak' is a hydrogen atom or a C$_3$–C$_6$ alkyl group optionally substituted with a hydroxy group, the nitrogen atom to which Ak' is attached may be optionally N-oxidized; and R' is a hydrogen atom, a C$_2$–C$_6$ alkyl group, a C$_3$–C$_6$ alkynyl group, a C$_3$–C$_7$ cycloalkyl group, or a C$_3$–C$_6$ cycloalkylmethyl group, and the hydrogen atom on the carbon atom for R' may be optionally substituted with a hydroxy group and the hydrogen atom on the indazole ring may be optionally substituted with a hydroxy group; and wherein the hydroxy and/or amino groups may be conjugated with glucuronic acid, sulfuric acid or glutathione.

Illustrative examples of the metabolites may include:
N-[endo-9-(n-Propyl)-3-oxa-9-azabicyclo[3.3.1]non-7-yl]-1H-indazole-3-carboxamide,
N-[endo-9-(n-butyl)-3-oxa-9-azabicyclo[3.3.1]non-7-yl]-1H-indazole-3-carboxamide,
N-[endo-9-(n-pentyl)-3-oxa-9-azabicyclo[3.3.1]non-7-yl]-1H-indazole-3-carboxamide,
N-[endo-9-(n-butyl)-3-oxa-9-azabicyclo[3.3.1]non-7-yl]-1-(4-hydroxy-1-methyl-2-butynyl)indazole-3-carboxamide,
N-[endo-9-(n-butyl)-3-oxa-9-azabicyclo[3.3.1]non-7-yl]-4-hydroxy-1-isopropylindazole-3-carboxamide,
N-[endo-9-(n-butyl)-3-oxa-9-azabicyclo[3-3-1]non-7-yl]-1-(sec-butyl)-4-hyroxyindazole-3-carboxamide,
(S)-(+)-N-[endo-9-(n-butyl)-3-oxa-9-azabicyclo[3.3.1]non-7-yl]-1-(sec-butyl)-4-hydroxyindazole-3-carboxamide,
N-[endo-9-(n-butyl)-3-oxa-9-azabicyclo[3.3.1]non-7-yl]-5-hydroxy-1-isopropylindazole-3-carboxamide,
N-[endo-9-(n-butyl)-3-oxa-9-azabicyclo[3.3.1]non-7-yl]-1-(sec-butyl)-5-hydroxyindazole-3-carboxamide,
(S)-(+)-N-[endo-9-(n-butyl)-3-oxa-9-azabicyclo[3.3.1]non-7-yl]-1-(sec-butyl)-5-hydroxyindazole-3-carboxamide,
N-[endo-9-(n-butyl)-3-oxa-9-azabicyclo[3.3.1]non-7-yl]-6-hydroxy-1-isopropylindazole-3-carboxamide,
N-[endo-9-(n-butyl)-3-oxa-9-azabicyclo[3.3.1]non-7-yl]-1-(sec-butyl)-6-hydroxyindazole-3-carboxamide,
(S)-(+)-N-[endo-9-(n-butyl)-3-oxa-9-azabicyclo[3.3.1]non-7-yl]-1-(sec-butyl)-6-hydroxyindazole-3-carboxamide,
N-[endo-9-(n-butyl)-3-oxa-9-azabicyclo[3.3.1]non-7-yl]-7-hydroxy-1-isopropylindazole-3-carboxamide,
N-[endo-9-(n-butyl)-3-oxa-9-azabicyclo[3.3.1]non-7-yl]-1-(sec-butyl)-7-hydroxyindazole-3-carboxamide,
(S)-(+)-N-[endo-9-(n-butyl)-3-oxa-9-azabicyclo[3.3.1]non-7-yl]-1-(sec-butyl)-7-hydroxyindazole-3-carboxamide,
N-[endo-3-oxa-9-azabicyclo[3.3.1]non-7-yl]-1-isopropylindazole-3-carboxamide,
N-[endo-3-oxa-9-azabicyclo[3.3.1]non-7-yl]-1-(sec-butyl)-indazole-3-carboxamide,
(S)-(+)-N-[endo-3-oxa-9-azabicyclo[3.3.1]non-7-yl]-1-(sec-butyl)indazole-3-carboxamide,
endo-9-(n-butyl)-7-(1-isopropylindazole-3-carbonylamino)-3-oxa-9-azabicyclo[3.3.1]nonane 9-oxide,
endo-9-(n-butyl)-7-[1-(sec-butyl)indazole-3-carbonylamino]-3-oxa-9-azabicyclo[3.3.1]nonane 9-oxide,
(S)-(+)-endo-9-(n-butyl)-7-[1-(sec-butyl)indazole-3-carbonylamino]-3-oxa-9-azabicyclo[3.3.1]nonane 9-oxide,
N-[endo-3-oxa-9-azabicyclo[3.3.1]non-7-yl]-4-hydroxy-1-isopropylindazole-3-carboxamide,
N-[endo-3-oxa-9-azabicyclo[3.3.1]non-7-yl]-1-(sec-butyl)-4-hydroxyindazole-3-carboxamide,
(S)-(+)-N-[endo-3-oxa-9-azabicyclo[3.3.1]non-7-yl]-1-(sec-butyl)-4-hydroxyindazole-3-carboxamide,
N-[endo-3-oxa-9-azabicyclo[3.3.1]non-7-yl]-5-hydroxy-1-isopropylindazole-3-carboxamide,
N-[endo-3-oxa-9-azabicyclo[3.3.1]non-7-yl]-1-(sec-butyl)-5-hydroxyindazole-3-carboxamide,
(S)-(+)-N-[endo-3-oxa-9-azabicyclo[3.3.1]non-7-yl]-1-(sec-butyl)-5-hydroxyindazole-3-carboxamide,
N-[endo-3-oxa-9-azabicyclo[3.3.1]non-7-yl]-6-hydroxy-1-isopropylindazole-3-carboxamide,
N-[endo-3-oxa-9-azabicyclo[3.3.1]non-7-yl]-1-(sec-butyl)-6-hydroxyindazole-3-carboxamide,
(S)-(+)-N-[endo-3-oxa-9-azabicyclo[3.3.1]non-7-yl]-1-(sec-butyl)-6-hydroxyindazole-3-carboxamide,
N-[endo-3-oxa-9-azabicyclo[3.3.1]non-7-yl]-7-hydroxy-1-isopropylindazole-3-carboxamide, N-[endo-3-oxa-9-azabicyclo[3.3.1]non-7-yl]-1-(sec-butyl)-7-hydroxyindazole-3-carboxamide,
(S)-(+)-N-[endo-3-oxa-9-azabicyclo[3.3.1]non-7-yl]-1-(sec-butyl)-7-hydroxyindazole-3-carboxamide,
N-[endo-9-(n-butyl)-3-oxa-9-azabicyclo[3.3.1]non-7-yl]-1H-4-hydroxyindazole-3-carboxamide,
N-[endo-9-(n-butyl)-3-oxa-9-azabicyclo[3.3.1]non-7-yl]-1H-5-hydroxyindazole-3-carboxamide,
N-[endo-9-(n-butyl)-3-oxa-9-azabicyclo[3.3.1]non-7-yl]-1H-6-hydroxyindazole-3-carboxamide, and
N-[endo-9-(n-butyl)-3-oxa-9-azabicyclo[3.3.1]non-7-yl]-1H-7-hydroxyindazole-3-carboxamide,
as well as their conjugates with glucuronic acid, sulfuric acid, glutathione or the like.

The compounds of formula (I) may be converted, if desired, to the corresponding acid addition salts with pharmaceutically acceptable acids. The acid addition salts are included within the scope of this invention, which include, for example, the salts with inorganic acids such as hydrochloric acid, hydrobromic acid, sulfuric acid, phosphoric acid, and the like or the salts with organic acids such as acetic acid, succinic acid, oxalic acid, malic acid, tartaric acid, fumaric acid, citric acid, malonic acid, lactic acid, methanesulfonic acid, p-toluenesulfonic acid, mandelic acid, suberic acid or the like.

The invention also provides a 5-HT$_4$ receptor agonist, which comprises as an active ingredient a compound of formula (I) or a pharmaceutically acceptable salt thereof.

The invention further provides a pharmaceutical composition comprising as an active ingredient a compound of formula (I) or a pharmaceutically acceptable salt thereof, and a pharmaceutically acceptable carrier.

The compounds of the invention can usually be administered orally or parenterally in the form of a pharmaceutical preparation. The pharmaceutical preparations include e.g. tablets, powders, granules, sugar-coated tablets, hard and soft capsules, solutions, emulsions and suspensions for oral administration and injections for parenteral administration. These preparations can be prepared by conventional methods employing conventional additives such as excipients, stabilizers, antioxidants, solubilizers, wetting agents, emulsifiers, lubricants, colorants, flavorings, buffers, preservatives or the like.

Route and dosage of administration for the compounds of the invention are not specifically limited and are appropriately chosen depending upon form of the formulation, age and sex of the patient, severity of the disease and other factors. Daily dosage of the active ingredient is 0.001 to 200 mg. No adverse toxicological effects are indicated at any of the above dosage ranges.

The invention is further illustrated by the following examples.

PREPARATION EXAMPLE 1-1

3-Oxa-1,5-pentanedial

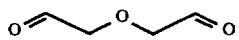

Into a solution of 2,5-dihydrofuran(20 g) in methanol(200 ml) was bubbled an ozone gas at −78° C. for 6 hours. Thereafter, a nitrogen gas was introduced at that temperature for 30 minutes, dimethyl sulfide (46.1 ml) was added dropwise over 15 minutes and the mixture was stirred for 30 minutes. The reaction solution was allowed to be raised to −30° C. and then stirred for 30 minutes, at 0° C. for 30 minutes and then at room temperature for 30 minutes. The solvent was distilled off under reduced pressure to afford crude 3-oxa-1,5-pentanedial. This product was employed for the subsequent reaction without any purification.

PREPARATION EXAMPLE 1-2

3-Oxa-1,5-pentanedial

An aqueous solution of 3,4-dihydroxytetrahydrofuran was stirred under ice-cooling, an aqueous solution of sodium periodate was added dropwise and the mixture was then stirred for 3 hours. The precipitate was filtered with Celite and the filtrate was employed for the subsequent reaction without any purification.

PREPARATION EXAMPLE 2

9-(n-Butyl)-3-oxa-9-azabicyclo[3.3.1]nonan-7-one

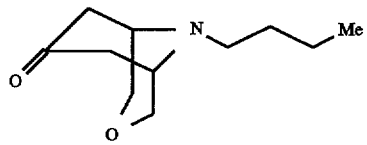

To a solution of sodium dihydrogenphospate (123.1 g) and citric acid (31.1 g) in water (3000 ml) were added in turn n-butylamine (35.5 g) and acetonedicarboxylic acid (77.0 g) and pH was adjusted to 4.6 with a 10% aqueous solution of sodium hydroxide. To the reaction solution was added dropwise at room temperature a solution of the crude aldehyde (23 g) in methanol (20 ml) and the mixture was stirred for 65 hours. Then, a 10% aqueous solution of potassium hydroxide (300 ml) was added to the reaction solution and extracted five times with chloroform. The combined organic layer was washed with a 10% aqueous solution of sodium hydroxide (200 ml), dried over potassium carbonate and the solvent was distilled off under reduced pressure. The residue was purified by a silica gel column chromatography (ethyl acetate) to give 9-(n-butyl)-3-oxa-9-azabicyclo[3.3.1]nonan-7-one (28.2 g).

$^1$H NMR(CDCl$_3$) δ 0.95(t, J=7 Hz, 3H), 1.35–1.45(m, 2H), 1.47–1.54(m, 2H), 2.28(d, J=16 Hz, 2H), 2.66(dd, J=5 Hz, J=14 Hz, 2H), 2.68(t, J=7 Hz, 2H), 3.19(d, J=6 Hz, 2H), 3.71(d, J=11 Hz, 2H), 3.79(d, J=11 Hz, 2H)

The following compounds were prepared in a similar manner.

9-(n-Propyl)-3-oxa-9-azabicyclo[3.3.1]nonan-7-one $^1$H NMR(CDCl$_3$) δ 0.97(t, J=7 Hz, 3H), 1.54(sext, J=7 Hz, 2H), 2.29(d, J=15 Hz, 2H), 2.65(t, J=7 Hz, 2H), 2.66(dd, J=6 Hz, 15 Hz 2H), 3.18(d, J=6 Hz, 2H), 3.71(d, J=11 Hz, 2H), 3.79(d, J=11 Hz, 2H)

9-(n-Pentyl)-3-oxa-9-azabicyclo[3.3.1]nonan-7-one $^1$H NMR(CDCl$_3$) δ 0.92(t, J=7 Hz, 3H), 1.24–1.36(m, 4H), 1.37–1.54(m, 2H), 2.28(d, J=16 Hz, 2H), 2.65(dd, J=6 Hz, 14 Hz, 2H), 2.68(t, J=7 Hz, 2H), 3.19(d, J=5 Hz, 2H), 3.71(d, J=11 Hz, 2H), 3.78(d, J=11 Hz, 2H)

PREPARATION EXAMPLE 3

9-(n-Butyl)-3-oxa-9-azabicyclo[3.3.1]nonan-7-one oxime

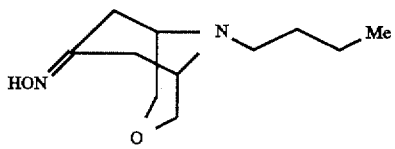

To a solution of 9-(n-butyl)-3-oxa-9-azabicyclo-[3.3.1]-nonan-7-one (28 g) in ethanol (150 ml) were added in turn pyridine (18.0 ml) and hydroxylamine hydrochloride (11.9 g) and the mixture was heated under reflux for 40 minutes. To the reaction solution were added water (29 ml) and potassium carbonate (57.9 g), the mixture was stirred for 30 minutes and dried over potassium carbonate. The solvent was distilled off under reduced pressure to give the crude 9-(n-butyl)-3-oxa-9-azabicyclo[3.3.1]nonan-7-one oxime. This product was employed for the sebsequent reaction without any purification.

The following compounds were prepared in a similar manner.

9-(n-Propyl)-3-oxa-9-azabicyclo[3.3.1]nonan-7-one oxime and 9-(n-Pentyl)-3-oxa-9-azabicyclo[3.3.1] nonan-7-one oxime

PREPARATION EXAMPLE 4-1 endo-7-Amino-9-(n-butyl)-3-oxa-9-azabicyclo[3.3.1] nonane

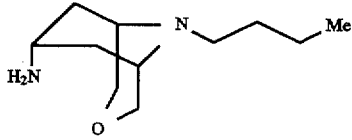

To a solution of 9-(n-butyl)-3-oxa-9-azabicyclo-[3.3.1] nonan-7-one oxime (33.0 g) in ethanol (300 ml) were added in turn ammonium acetate (97 g) and an ethanolic suspension of Raney nickel (15 ml) and the mixture was stirred in an autoclave at 70° C. under hydrogen atmosphere of 50 kg/cm$^2$ for 7 hours. The reaction solution was filtered with Celite and the filtrate was distilled under reduced pressure to remove the solvent. To the residue was added a 30% aqueous solution of sodium hydroxide (100 ml). The mixture was extracted three times with chloroform and the combined organic layer was dried over potassium carbonate and the solvent was distilled off under reduced pressure to give the crude endo-7-amino-9-(n-butyl)-3-oxa-9-azabicyclo[3.3.1] nonane (27.0 g). This product was employed for the subsequent reaction without any purification.

$^1$H NMR(CDCl$_3$) δ 0.92(t, J=7 Hz, 3H), 1.33(d, J=15 Hz, 2H), 1.34–1.37(m, 4H), 2.38(td, J=7 Hz, 15 Hz, 2H), 2.59(t, J=7 Hz, 2H), 2.66(bs, 2H), 3.16(t, J=7 Hz, 1H), 3.70(d, J=11 Hz, 2H), 3.87(d, J=11 Hz, 2H)

The following compounds were prepared in a similar manner.

endo-7-Amino-9-(n-propyl)-3-oxa-9-azabicyclo [3.3.1]nonane $^1$H NMR(CDCl$_3$) δ 0.91(t, J=8 Hz, 3H), 1.33(d, J=15 Hz, 2H), 1.42(sext, J=8 Hz, 2H), 2.38(td, J=6 Hz, 15 Hz, 2H), 2.44(bs, 2H), 2.56(t, J=8 Hz, 2H), 2.65(d, J=4 Hz, 2H), 3.16(t, J=7 Hz, 1H), 3.70(d, J=11 Hz, 2H), 3.87(d, J=11 Hz, 2H)

endo-7-Amino-9-(n-pentyl)-3-oxa-9-azabicyclo [3.3.1]nonane $^1$H NMR(CDCl$_3$) δ 0.90(t, J=7 Hz, 3H), 1.28–1.43(m, 8H), 2.30(bs, 2H), 2.58(t, J=7 Hz, 2H), 2.66(d, J=4 Hz, 2H), 3.16(t, J=7 Hz, 1H), 3.70(d, J=11 Hz, 2H), 3.88(d, J=11 Hz, 2H)

PREPARATION EXAMPLE 4-2 endo-7-Amino-9-(n-butyl)-3-oxa-9-azabicyclo[3.3.1] nonane

A mixture of 9-(n-butyl)-3-oxa-9-azabicycl[3.3.1]-nonan-7-one, Raney nickel and aqueous ammonia was stirred in an autoclave at 70° C. for 8 hours under a hydrogen gas atmosphere of 50 kg/cm$^2$ to give the title compound. This product was employed for the subsequent reaction without any purification.

PREPARATION EXAMPLE 5

N-[endo-9-(n-Butyl)-3-oxa-9-azabicyclo[3.3.1]non-7-yl]-1H-indazole-3-carboxamide

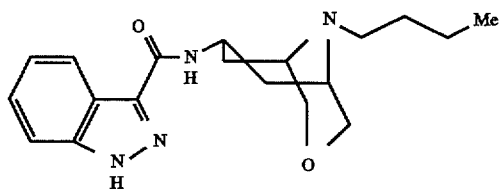

To a DMF solution (400 ml) of endo-7-amino-9-(n-butyl)-3-oxa-9-azabicyclo[3.3,1]nonane (20.0 g) were added in turn potassium carbonate (20.7 g), dimethylaminopyridine (7.3 g) and diindazolo[2,3-a][2',3'-d]pyrazine-7,14-dione (14.2 g) under ice-cooling and the mixture was stirred for 3.5 hours. The reaction solution was pourd into water (1000 ml) and extracted three times with ethyl acetate. The combined organic layer was washed with saturated saline, dried over potassium carbonate and concentrated under reduced pressure. The residue was recrystallized from ethanol to give the title compound (18.4 g).

$^1$H NMR(CDCl$_3$) δ 0.94(t, J=7 Hz, 3H), 1.34–1.46(m, 4H), 1.51(d, J=15 Hz, 2H), 2.47(td, J=6 Hz, 15 Hz, 2H), 2.67(t, J=7 Hz, 2H), 2.76(bs, 2H), 3.88(d, J=11 Hz, 2H), 4.03(d, J=11 Hz, 2H), 4.78(td, J=7 Hz, 11 Hz, 1H), 7.26–7.31(m, 2H), 7.42(t, J=7 Hz, 1H), 7.50(d, J=8 Hz, 1H), 8.44(d, J=8 Hz, 1H), 9.59(d, J=8 Hz, 1H), 10.23(bs, 1H) m.p. 255–275° C.

The title compound was dissolved in a mixed solvent of methanol and chloroform and a 4N hydrochloric acid/ethyl acetate solution was added under ice-cooling. After the solvent was distilled off, the crystalline precipitated from methanol/ethyl acetate was recovered by filtration and dried under reduced pressure to afford the corresponding hydrochloride.

$^1$H NMR(DMSO-d$_6$) δ 0.96(t, J=7 Hz, 3H), 1.38(q, J=8 Hz, 2H), 1.62–1.72(m, 2H), 1.77–2.04(m, 4H), 2.57–2.89 (m, 2H), 3.17–3.44(m, 2H), 3.88–4.12(m, 2H), 4.26(d, J=12 Hz, 2H), 4.63(q, J=9 Hz, 1H), 7.23(t, J=8 Hz, 2H), 7.40(t, J=8 Hz, 1H), 7.60(d, J=9 Hz, 1H), 8.18(d, J=8 Hz, 1H), 8.95(t, J=13 Hz, 1H)

m.p. 262°–270° C.

The following compounds were prepared in a similar manner.

N-[endo-9-(n-Propyl)-3-oxa-9-azabicyclo[3.3.1]non-7-yl]-1H-indazole-3-carboxamide $^1$H NMR(CDCl$_3$) δ 0.94(t, J=7 Hz, 3H), 1.47(sext, J=7 Hz, 2H), 1.51(d, J=15 Hz, 2H), 2.47(td, J=6 Hz, 15 Hz, 2H), 2.64(t, J=7 Hz, 2H), 2.75(bs, 2H), 3.88(d, J=11 Hz, 2H), 4.03(d, J=11 Hz, 2H), 4.79(td, J=7 Hz, 11 Hz, 1H), 7.25–7.30(m, 1H), 7.41(dt, J=1 Hz, 8 Hz, 1H), 7.51(dd, J=1 Hz, 8 Hz, 1H), 8.44(dd, J=1 Hz, 8 Hz, 1H), 9.58(d, J=11 Hz, 1H), 10.37(bs, 1H)

N-[endo-9-(n-Pentyl)-3-oxa-9-azabicyclo[3.3.1]non-7-yl]-1H-indazole-3-carboxamide $^1$H NMR(CDCl$_3$) δ 0.91(t, J=7 Hz, 3H), 1.31–1.35(m, 4H), 1.37–1.46(m, 2H), 1.50(d, J=15 Hz, 2H), 2.47(td, J=6 Hz, 16 Hz, 2H), 2.67(t, J=7 Hz, 2H), 3.87(d, J=11 Hz, 2H), 4.02(d, J=11 Hz, 2H), 4.78(td, J=7 Hz, 11 Hz, 1H), 7.26–7.31(m, 1H), 7.42(t, J=7 Hz, 1H), 7.50(d, J=8 Hz, 1H), 8.44(d, J=8 Hz, 1H), 9.59(d, J=11 Hz, 1H), 10.15(bs, 1H)

PREPARATION EXAMPLE 6

5-Benzyloxy-2-nitrotoluene

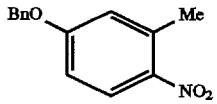

To a solution of 4-nitro-m-cresol (100.0 g) in methylene chloride (1000 ml) was added a 1N aqueous solution of sodium hydroxide (1000 ml). To the resulting two-layer solution were added in turn benzyl bromide (170 ml) and tetra-n-butylammonium bromide (2.17 g) while stirring at room temperature. After stirring at room temperature overnight, the reaction solution was placed into a separating funnel to separate the organic layer from the aqueous layer. The aqueous layer was extracted with methylene chloride. The combined organic layer was washed with saturated saline, dried over magnesium sulfate and the solvent was distilled off to give a yellow oily substance. The solidified yellow oily substance was ground in hexane, filtered and dried. The resulting yellow powder was recrystallized from an ethyl acetate/hexane mixed solvent system to give the title compound (116.7 g).

$^1$H NMR(DMSO-d$_6$) δ 2.61(s, 3H), 5.12(s, 2H), 6.84–6.87(m, 2H), 7.33–7.41(m, 5H), 2.67(t, J=7 Hz, 2H), 8.04–8.06(m, 1H)

The following compound was prepared in a similar manner.

3-Benzyloxy-2-nitrotoluene $^1$H NMR(CDCl$_3$) δ 2.31(s, 3H), 5.15(s, 2H), 6.84–6.89 (m, 2H), 7.22–7.37(m, 6H)

PREPARATION EXAMPLE 7

5-Benzyloxy-2-nitrophenylacetic acid

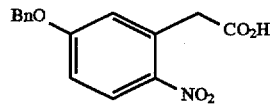

To a suspension of sodium methoxide (13.3 g) in ethyl ether (250 ml) were added in turn ethyl formate (33.0 g) and 4-benzyloxy-2-nitrotoluene (50.0 g) and the mixture was heated under reflux for 6 hours. The solvent was distilled off under reduced pressure, the resulting residue was dissolved in water and 10% hydrogen peroxide and 10N aqueous sodium hydroxide solution were added in turn. Insolubles were filtered off with Celite and the filtrate was adjusted to pH 2 with conc. hydrochloric acid under ice-cooling. The precipitated yellow solid was recovered by filtration, washed with water and dried to give the title compound (25.1 g).

$^1$H NMR(CD$_3$OD) δ 6 4.01(s, 2H), 7.04–7.09(m, 2H), 7.30–7.45(m, 5H), 8.16(d, J=9 Hz, 2H)

The following compound was prepared in a similar manner.

3-Benzyloxy-2-nitrophenylacetic acid $^1$H NMR(CDCl$_3$) δ 3.68(s, 2H), 5.16(s, 2H), 6.94(d, J=8 Hz, 2H), 7.00(d, J=8 Hz, 2H), 7.31–7.37(m, 6H)

PREPARATION EXAMPLE 8

Isopropyl 5-benzyloxy-2-nitrophenylacetate

To a solution of 5-benzyloxy-2-nitrophenylacetic acid (25.1 g) in methylene chloride (250 ml) were added in turn 2-propanol (27 ml), 4-dimethylaminopyridine (1.07 and 1-ethyl-3-(3-dimethylaminopropyl)carbodiimide hydrochloride (18.4 g) and the resulting mixture was stirred at room temperature for one hour and then allowed to stand overnight. After the solvent was distilled off under reduced pressure, the resulting residue was diluted with ethyl acetate, washed subsequently with 1N hydrochloric acid and saturated saline. The organic layer was dried over magnesium sulfate and distilled off under reduced pressure. The dark yellow oily substance thus obtained (29.7 g) was purified by a silica gel column chromatography (hexane:ethyl acetate= 4:1) to give the title compound (22.5 g).

$^1$H NMR(CDCl$_3$) δ 1.25(d, J=6 Hz, 6H), 3.95(s, 2H), 5.04(quint, J=6 Hz, 1H), 5.14(s, 2H), 6.88(d, J=3 Hz, 1H), 6.97(dd, J=3 Hz, 9 Hz, 1H), 7.30–7.42(m, 5H), 8.19(d, J=9 Hz, 1H)

The following compound was prepared in a similar manner.

Isopropyl 3-benzyloxy-2-nitrophenylacetate $^1$H NMR(CDCl$_3$) δ 1.23(d, J=6 Hz, 6H), 3.63(s, 2H), 5.02(quint, J=6 Hz, 1H), 5.18(s, 2H), 6.95(d, J=8 Hz, 1H), 7.00(d, J=8 Hz, 1H), 7.31–7.40(m, 6H)

PREPARATION EXAMPLE 9

Isopropyl 5-benzyloxy-2-aminophenylacetate

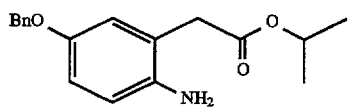

A mixture of ammonium chloride (5.63 g), a water/ethanol mixed solvent (1:1 v/v, 240 ml) and powdery iron (29.3 g) was heated under reflux for one hour and a Soxhlet extractor containing isopropyl 5-benzyloxy-2-nitrophenylacetate was set and refluxing was continued for a further 3 hours and then allowed to stand at room temperature overnight. Insolubles were filtered off with Celite and the solvent was distilled off under reduced pressure. The residue thus obtained was dissolved in ethyl ether, and the solution was washed with water, dried over magnesium sulfate and concentrated under reduced pressure. The oily substance thus obtained (18.9 g) was purified by a silica gel column chromatography (hexane:ethyl acetate=4:1) to give the title compound (10.8 g).

$^1$H NMR(CDCl$_3$) δ 1.22(d, J=6 Hz, 6H), 3.50(s, 2H), 3.82(bs, 2H), 4.95–5.01(m, 3H), 6.66(d, J=8 Hz, 1H), 6.74–6.78(m, 2H), 7.30–7.42(m, 5H)

The following compound was prepared in a similar manner.

Isopropyl 3-benzyloxy-2-aminophenylacetate $^1$H NMR(CDCl$_3$) δ 1.22(d, J=6 Hz, 6H), 3.55(s, 2H), 4.31(bs, 2H), 4.99(quint, J=6 Hz, 1H), 5.07(s, 2H), 6.68(t, J=8 Hz, 1H), 6.75–6.82(m, 2H), 7.32–7.45(m, 5H)

PREPARATION EXAMPLE 10

Isopropyl 1-acetyl-5-benzyloxyindazole-3-carboxylate

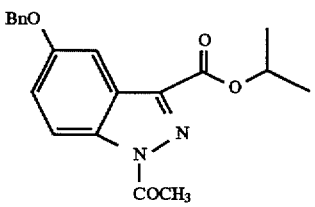

To a solution of isopropyl 5-benzyloxy-2-aminophenylactate (13.2 g) in benzene (140 ml) were added potassium acetate (4.33 g) and then acetic anhydride (13.5 g) and the mixture was heated under reflux for 20 minutes. A solution of isopentyl nitrite (7.76 g) in benzene (30 ml) was added dropwise over 5 minutes under reflux and then refluxing was continued for further 3 hours. After allowing to cool to room temperature, insolubles were filtered off with Celite and concentrated under reduced pressure. The resulting residue (16.9 g) was purified by a silica gel column chromatography (hexane:ethyl acetate=9:1–4:1) to give the title compound (10.9 g).

$^1$H NMR(CDCl$_3$) δ 1.47(d, J=6 Hz, 6H), 2.84(s, 3H), 5.16(s, 2H), 5.39(quint, J=6 Hz, 1H), 7.29(dd, J=2 Hz, 9 Hz, 1H), 7.34–7.48(m, 5H), 7.63(d, J=2 Hz, 1H), 8.35(d, J=9 Hz, 1H)

The following compound was prepared in a similar manner.

Isopropyl 1-acetyl-7-benzyloxyindazole-3-carboxylate $^1$H NMR(CDCl$_3$) δ 1.47(d, J=6 Hz, 6H), 2H), , 3H), 5.29(s, 2H), 5.41(quint, J=6 Hz, 1H), 7.08(d, J=8 Hz, 1H), 7.31–7.43(m, 4H), 7.57(d, J=8 Hz, 1H), 7.81(d, J=7 Hz, 1H)

PREPARATION EXAMPLE 11

1H-5-Benzyloxyindazole-3-carboxylic acid

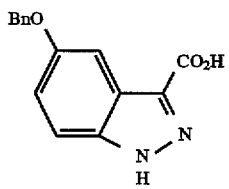

To a solution of isopropyl 1-acetyl-5-benzyloxyindazole-3-carboxylate (10.6 g) in methanol (200 ml) was added a 10N aqueous solution of potassium hydroxide (30 ml) and the mixture was heated under reflux for 10 hours. The reaction solution was concentrated under reduced pressure and the resulting residue was mixed with water and adjusted to pH 1 with the addition of 5N hydrochloric acid. The precipitate was recovered by filtration, washed with water and dried to give the title compound (8.26 g). This compound was provided for the subsequent reaction without any purification.

$^1$H NMR(DMSO-d$_6$) δ 5.11(s, 2H), 7.01(dd, J=2 Hz, 9 Hz, 1H), 7.30–7.49(m, 6H), 7.67(d, J=2 Hz, 1H)

The following compound was prepared in a similar manner.

1H-7-Benzyloxyindazole-3-carboxylic acid $^1$H NMR(CDCl$_3$) δ 5.11(s, 2H), 7.01(dd, J=2 Hz, 9 Hz, 1H), 7.30–7.49(m, 6H), 7.67(d, J=2 Hz, 1H)

Example 1

N-[endo-9-(n-Butyl)-3-oxa-9-azabicyclo[3.3.1]non-7-yl]-1-(n-propyl)indazole-3-carboxamide

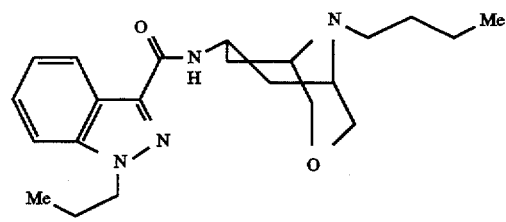

To a solution of N-[endo-9-(n-butyl)-3-oxa-9-azabicyclo[3.3.1]non-7-yl]-1H-indazole-3-carboxamide (0.68 g) in DMF (20 ml) was added 60% sodium hydride (0.10 g) under ice-cooling. After stirring under ice-cooling for 30 minutes and at room temperature for one hour, 1-bromopropane (0.32 g) was added and the stirring was continued for 3.5 hours. The reaction solution was poured into water (100 ml) and extracted three times with ethyl acetate. The combined organic layer was washed with saturated saline, dried over potassium carbonate, and concentrated under reduced pressure. The residue was purified by a silica gel column chromatography (methanol:chloroform=1:10) and recrystallized (from hexane-ether solvent system) to give, the title compound (0.47 g).

¹H NMR(CDCl₃) δ 0.94(t, J=7 Hz, 6H), 1.35–1.41(m, 4H), 1.50(d, J=15 Hz, 2H), 1.97(sext, J=7 Hz, 2H), 2.46(td, J=6 Hz, 15 Hz, 2H), 2.66(t, J=7 Hz, 2H), 2.74(bs, 2H), 3.86(d, J=11 Hz, 2H), 4.00(d, J=10 Hz, 2H), 4.35(t, J=7 Hz, 2H), 4.78(td, J=7 Hz, 10 Hz, 1H), 7.22–7.26(m, 1H), 7.36–7.42(m, 2H), 8.38(d, J=8 Hz, 1H), 9.39(d, J=10 Hz, 1H)

The title compound was dissolved in chloroform and a 4N hydrochloric acid/ethyl acetate solution was added under ice cooling. After the solvent was distilled off, the crystal precipitated from methanol/ethyl acetate was recovered by filtration and dried under reduced pressure to give the hydrochloride.

m.p. 211°–212° C.

The following compounds were prepared in a similar manner.

Example 2

N-[endo-9-(n-Propyl)-3-oxa-9-azabicyclo[3.3.1]non-7-yl]-1-isopropyl-indazole-3-carboxamide

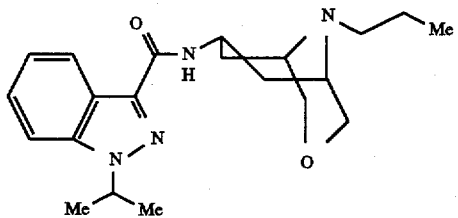

¹H NMR(CDCl₃) δ 0.95(t, J=7 Hz, 3H), 1.47(sext, J=7 Hz, 2H), 1.50(d, J=15 Hz, 2H), 1.60(d, J=7 Hz, 6H), 2.46(td, J=6 Hz, 15 Hz, 2H), 2.64(t, J=7 Hz, 2H), 2.73(bs, 2H), 3.85(d, J=11 Hz, 2H), 4.00(d, J=11 Hz, 2H), 4.77(td, J=7 Hz, 11 Hz, 1H), 4.85(sept, J=7 Hz, 1H), 7.22–7.26(m, 1H), 7.37(dt, J=1 Hz, 7Hz, 1H), 7.44(d, J=8 Hz, 1H), 8.38(d, J=8 Hz, 1H), 9.50(d, J=11 Hz, 1H)

The title compound was converted to the hydrochloride in accordance with the procedure described in Example 1.

Example 3

N-[endo-9-(n-Propyl)-3-oxa-9-azabicyclo[3.3.1]non-7-yl]-1-(3-pentyl)-indazole-3-carboxamide

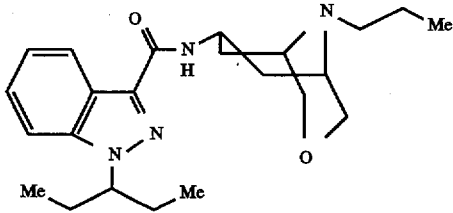

¹H NMR(CDCl₃) δ 0.79(t, J=7 Hz, 6H), 0.94(t, J=7 Hz, 3H), 1.42–1.48(m, 2H), 1.50(d,m J=15 Hz, 2H), 1.86–1.96 (m, 2H), 2.05–2.14(m, 2H), 2.45(td, J=6 Hz, 15 Hz, 2H), 2.63(t, J=7 Hz, 2H), 2.73(bs, 2H), 3.82(d, J=11 Hz, 2H), 3.99(d, J=11 Hz, 2H), 4.27–4.32(m, 1H), 4.76(td, J=7 Hz, 11 Hz, 1H), 7.21–7.24(m, 1H), 7.36(dt, J=1Hz, 7 Hz, 1H), 7.42(d, J=9 Hz, 1H), 8.38(d, J=9 Hz, 1H), 9.52(d, J=11 Hz, 1H)

The title compound was converted to the hydrochloride in accordance with the procedure described in Example 1.

Example 4

N-[endo-9-(n-Butyl)-3-oxa-9-azabicyclo[3.3.1]non-7-yl]-1-ethylindazole-3-carboxamide

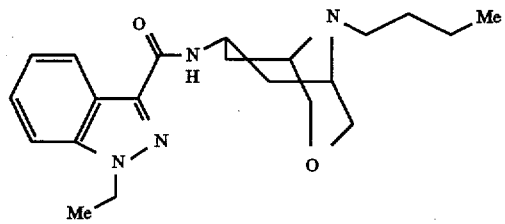

¹H NMR(CDCl₃) δ 0.94(t, J=7 Hz, 3H), 1.33–1.44(m, 4H), 1.50(d, J=15 Hz, 2H), 1.53(t, J=7 Hz, 3H), 2.46(td, J=6 Hz, 15 Hz, 2H), 2.67(t, J=7 Hz, 2H), 2.75(bs, 2H), 3.86(d, J=11 Hz, 2H), 4.00(d, J=11 Hz, 2H), 4.45(q, J=7 Hz, 2H), 4.78(td, J=7 Hz, 10 Hz, 1H), 7.23–7.27(m, 1H), 7.37–7.42 (m, 2H), 8.39(d, J=8 Hz, 1H), 9.39(d, J=10 Hz, 1H)

The title compound was converted to the hydrochloride in accordance with the procedure described in Example 1.

m.p. 225°–228° C.

Example 5

N-[endo-9-(n-Butyl)-3-oxa-9-azabicyclo[3.3.1]non-7-yl]-1-isopropyl-indazole-3-carboxamide

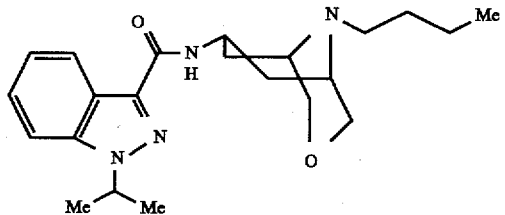

¹H NMR(CDCl₃) δ 0.94(t, J=7 Hz, 3H), 1.35–1.45(m, 4H), 1.50(d, J=15 Hz, 2H), 1.60(d, J=7 Hz, 6H), 2.46(td, J=6 Hz, 15 Hz, 2H), 2.67(t, J=7 Hz, 2H), 2.74(bs, 2H), 3.85(d, J=11 Hz, 2H), 3.99(d, J=11 Hz, 2H), 4.77(td, J=7 Hz, 11 Hz, 1H), 4.86(sept, J=7 Hz, 1H), 7.23–7.26(m, 1H), 7.37(t, J=7 Hz, 7.44(d, J=9 Hz, 1H), 8.38(d, J=8 Hz, 1H), 9.51(d, J=11 Hz, 1H)

Hydochloride

To N-[endo-9-(n-butyl)-3-oxa-9-azabicyclo-[3.3.1]non-7-yl]-1-isopropyl-indazole-3-carboxamide (0.50 was added 1.2N hydrogen chloride/2-propanol (3.7 ml) and the mixture was heated under reflux. After stirring at room temperature for 2 hours, the precipitated white crystal was recovered by filtration, dried under reduced pressure to give the hydrochloride of the title compound (0.45 g).

m.p. 232°–233° C.

¹H NMR(D₂O) δ 1.00(t, J=8 Hz, 3H), 1.48(sext, J=7 Hz, 2H), 1.59(d, J=6 Hz, 6H), 1.71–1.79(m 2H), 2.07–2.20(m, 2H), 2.78–2.91(m, 2H), 3.38–3.51(m, 2H), 3.70(d, J=4 Hz, 2H), 4.19–4.46(m, 4H), 4.74(t, J=7 Hz, 1H), 5.02–5.09(m, 1H), 7.41(t, J=8 Hz, 1H), 7.57(t, J=7 Hz, 1H), 7.76(d, J=9 Hz, 1H), 8.15(d, J=8 Hz, 1H)

Fumarate

N-[endo-9-(n-Butyl)-3-oxa-9-azabicyclo[3.3.1]non-7-yl]-1-isopropyl-indazole-3-carboxamide (0.49 g) and fumaric acid (0.15 g) were dissolved in hot ethanol (2 ml) and the solution was stirred at room temperature for 2 hours. The precipitated white crystal was recovered by filtration and dried under reduced pressure to give the fumarate of the title compound (0.53 g).

m.p. 164°–165° C.

$^1$H NMR(D$_2$O) δ 1.00(t, J=7 Hz, 3H), 1.48(sext, J=8 Hz, 2H), 1.60(d, J=7 Hz, 6H), 1.70–1.79(m, 2H), 2.10–2.18(m, 2H), 2.78–2.86(m, 2H), 3.42–3.48(m, 2H), 3.71(d, J=4 Hz, 2H), 4.20–4.45(m, 4H), 4.73(dt, J=2 Hz, 7 Hz, 1H), 5.03–5.10(m, 1H), 6.70(s, 2H), 7.41(t, J=7 Hz, 1H), 7.57(t, J=8 Hz, 1H), 7.77(d, J=8 Hz, 1H), 8.16(d, J=8 Hz, 1H)

Mesylate

Following the same procedure as the fumaric acid, the mesylate of the title compound was prepared from the ethanol/ethyl acetate solution.

m.p. 229°–238° C.

$^1$H NMR(D$_2$O) δ 0.99(t, J=7 Hz, 3H), 1.48(sext, J=7 Hz, 2H), 1.59(d, J=7 Hz, 6H), 1.74(quint, J=8 Hz, 2H), 2.05–2.22(m, 2H), 2.77–2.92(m, 2H), 2.82(s, 3H), 3.33–3.52(m, 2H), 3.69(d, J=3 Hz, 2H), 4.26–4.46(m, 4H), 4.73(t, J=7 Hz, 1H), 5.03–5.09(m, 1H), 7.40(t, J=7 Hz, 1H), 7.57(t, J=8 Hz, 1H), 7.76(d, J=8 Hz, 1H), 8.15(d, J=8 Hz, 1H)

Melonate

Following the same procedure as the fumaric acid, the melonate of the title compound was prepared from the 2-propanol solution.

m.p. 166°–167° C.

$^1$H NMR(D$_2$O) δ 1.00(t, J=7 Hz, 3H), 1.47(sext, J=7 Hz, 2H), 1.59(d, J=7 Hz, 6H), 1.70–1.78(m, 2H), 2.13(d, J=6 Hz, 2H), 2.78–2.85(m, 2H), 3.44(t, J=8 Hz, 2H), 3.70(d, J=7 Hz, 2H), 4.22–4.46(m, 4H), 4.73(t, J=7 Hz, 1H), 5.02–5.09(m, 1H), 7.40(t, J=8 Hz, 1H), 7.57(t, J=7 Hz, 1H), 7.76(d, J=9 Hz, 1H), 8.16(d, J=8 Hz, 1H)

Example 6

N-[endo-9-(n-Butyl)-3-oxa-9-azabicyclo[3.3.1]non-7-yl]-1-(n-butyl)-indazole-3-carboxamide

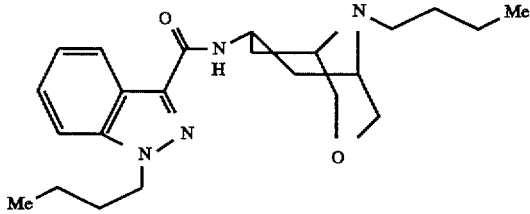

$^1$H NMR(CDCl$_3$) δ 0.92–0.96(m, 6H), 1.30–1.44(m, 6H), 1.51(d, J=15 Hz, 2H), 1.91(quint, J=7 Hz, 2H), 2.47(td, J=6 Hz, 14 Hz, 2H), 2.67(t, J=7 Hz, 2H), 2.75(bs, 2H), 3.86(d, J=11 Hz, 2H), 4.00(d, J=10 Hz, 2H), 4.39(t, J=7 Hz, 2H), 4.79(td, J=7 Hz, 11 Hz, 1H), 7.23–7.26(m, 1H), 7.36–7.41 (m, 2H), 8.38(d, J=8 Hz, 1H), 9.40(d, J=10 Hz, 1H)

The title compound was converted to the hydrochloride in accordance with the procedure described in Example 1.

m.p. 200°–210° C.

Example 7

N-[endo-9-(n-Butyl)-3-oxa-9-azabicyclo[3.3.1]non-7-yl]-1-isobutyl-indazole-3-carboxamide

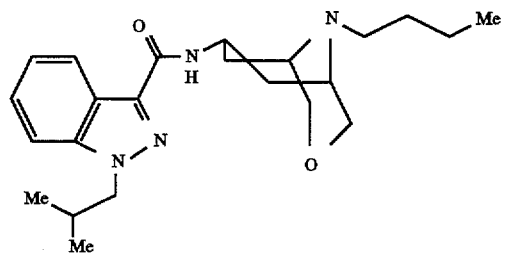

$^1$H NMR(CDCl$_3$) δ 0.93(d, J=7 Hz, 6H), 0.94(t, J=7 Hz, 3H), 1.33–1.46(m, 4H), 1.51(d, J=15 Hz, 2H), 2.30–2.38(m, 1H), 2.47(td, J=6 Hz, 15 Hz, 2H), 2.68(t, J=7 Hz, 2H), 2.75(bs, 2H), 3.85(d, J=11 Hz, 2H), 4.01(d, J=11 Hz, 2H), 4.18(d, J=7 Hz, 2H), 4.78(td, J=6 Hz, 10 Hz, 1H), 7.22–7.25 (m, 1H), 7.26–7.40 (m, 2H), 8.38(d, J=8 Hz, 1H), 9.40(d, J=11 Hz, 1H)

The title compound was converted to the hydrochloride in accordance with the procedure described in Example 1.

m.p. 216°–218° C.

Example 8

N-[endo-9-(n-Butyl)-3-oxa-9-azabicyclo[3.3.1non-7-yl]-1-(sec-butyl)-indazole-3-carboxamide

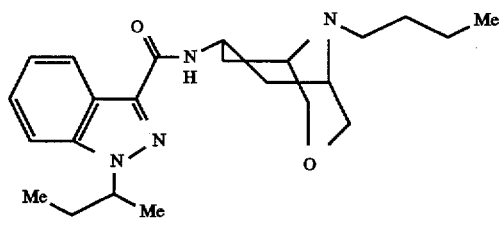

$^1$H NMR(CDCl$_3$) δ 0.80(t, J=7 Hz, 3H), 0.94(t, J=7 Hz, 3H), 1.34–1.45(m, 4H), 1.50(d, J=15 Hz, 2H), 1.58(d, J=6 Hz, 3H), 1.78–1.95(m, 1H), 2.05–2.14(m, 1H), 2.46(td, J=6 Hz, 15 Hz, 2H), 2.67(t, J=7 Hz, 2H), 2.74(bs, 2H), 3.84(d, J=11 Hz, 2H), 3.99(d, J=11 Hz, 2H), 4.54–4.60(m, 1H), 4.77(td, J=7 Hz, 11 Hz, 1H), 7.21–7.26(m, 1H), 7.36(t, J=7 Hz, 1H), 7.43(d, J=9 Hz, 1H), 8.38(d, J=8 Hz, 1H), 9.53(d, J=11 Hz, 1H)

The title compound was converted to the hydrochloride in accordance with the procedure described in Example 1.

m.p. 189°–191° C.

Example 9

N-[endo-9-(n-Butyl)-3-oxa-9-azabicyclo[3.3.1]non-7-yl]-1-(2-pentyl)-indazole-3-carboxamide

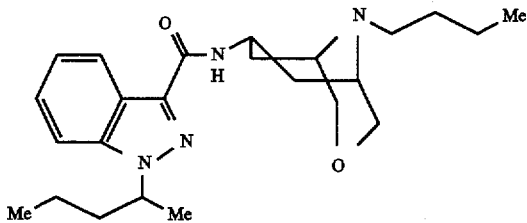

$^1$H NMR(CDCl$_3$) δ 0.86(t, J=8 Hz, 3H), 0.94(t, J=7 Hz, 3H), 1.09–1.25(m, 2H), 1.34–1.51(m, 4H), 1.50(d, J=15 Hz, 2H), 1.57(d, J=7 Hz, 3H), 1.76–1.84(m, 1H), 2.07–2.14(m, 1H), 2.46(td, J=6 Hz, 15 Hz, 2H), 2.67(t, J=7 Hz, 2H), 2.73(bs, 2H), 3.83(dd, J=3 Hz, 11 Hz, 2H), 3.99(d, J=11 Hz, 2H), 4.63–4.69(m, 1H), 4.76(td, J=7 Hz, 11 Hz, 1H), 7.21–7.25(m, 1H), 7.26–7.37 (m, 1H), 7.42(d, J=8 Hz, 1H), 8.38(d, J=8 Hz, 1H), 9.53(d, J=11 Hz, 1H)

The title compound was converted to the hydrochloride in accordance with the procedure described in Example 1.

m.p. 218°–222° C.

Example 10

N-[endo-9-(n-Butyl)-3-oxa-9-azabicyclo[3.3.1.]non-7-yl]-1-(3-pentyl)indazole-3-carboxamide

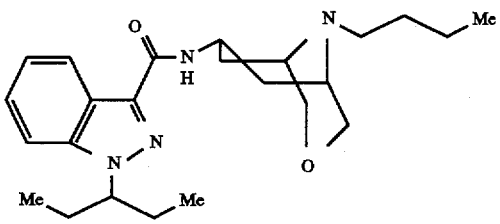

$^1$H NMR(CDCl$_3$) δ 0.74(t, J=7 Hz, 6H), 0.94(t, J=7 Hz, 3H), 1.34–1.45(m, 4H), 1.50(d, J=15 Hz, 2H), 1.86–1.96(m, 2H), 2.04–2.16(m, 2H), 2.46(td, J=6 Hz, 15 Hz, 2H), 2.67(t, J=7 Hz, 2H), 2.73(bs, 2H), 3.82(d, J=11 Hz, 2H), 3.99(d, J=11 Hz, 2H), 4.26–4.33(m, 1H), 4.76(td, J=7 Hz, 11 Hz, 1H), 7.21–7.26(m, 1H), 7.34–7.38(m, 1H), 7.42(d, J=9 Hz, 1H), 8.38(d, J=8 Hz, 1H), 9.52(d, J=11 Hz, 1H)

The title compound was converted to the hydrochloride in accordance with the procedure described in Example 1.

m.p. 207°–212° C.

Example 11

N-[endo-9-(n-Butyl)-3-oxa-9-azabicyclo[3.3.1]non-7-yl]-1-allyl-indazole-3-carboxamide

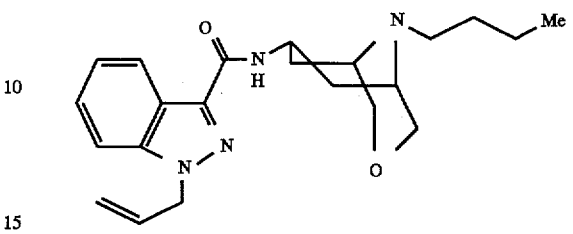

$^1$H NMR(CDCl$_3$) δ 0.94(t, J=7 Hz, 3H), 1.33–1.45(m, 4H), 1.50(d, J=15 Hz, 2H), 2.46(td, J=5 Hz, 15 Hz, 2H), 2.67(t, J=8 Hz, 2H), 2.75(bs, 2H), 3.86(d, J=11 Hz, 2H), 4.00(d, J=11 Hz, 2H), 4.78(td, J=7 Hz, 10 Hz, 1H), 5.05(dd, J=1 Hz, 6 Hz, 2H), 5.16(d, J=17 Hz, 1H), 5.24(d, J=10 Hz, 1H), 5.98–6.08(m, 1H), 7.24–7.28(m, 1H), 7.36–7.39(m, 2H), 8.39(d, J=8 Hz, 1H), 9.37(d, J=9 Hz, 1H)

The title compound was converted to the hydrochloride in accordance with the procedure described in Example 1.

m.p. 235°–237° C.

Example 12

N-[endo-9-(n-Butyl)-3-oxa-9-azabicyclo[3.3.1]non-7-yl]-1-(3-methyl-2-butenyl)indazole-3-carboxamide

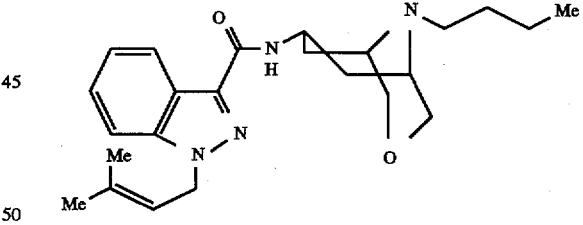

$^1$H NMR(CDCl$_3$) δ 0.94(t, J=7 Hz, 3H), 1.33–1.45(m, 4H), 1.50(d, J=15 Hz, 2H), 1.75(s, 3H), 1.88(s, 3H), 2.46(td, J=6 Hz, 15 Hz, 2H), 2.67(t, J=7 Hz, 2H), 2.74(bs, 2H), 3.85(d, J=11 Hz, 2H), 3.99(d, J=11 Hz, 2H), 4.78(td, J=7 Hz, 11 Hz, 1H), 5.01(d, J=7 Hz, 2H), 5.41–5.44(m, 1H), 7.22–7.26(m, 1H), 7.34–7.37(m, 2H), 8.37(d, J=8 Hz, 1H), 9.38(d, J=11 Hz, 1H)

The title compound was converted to the hydrochloride in accordance with the procedure described in Example 1.

m.p. 208°–210° C.

Example 13

N-[endo-9-(n-Butyl)-3-oxa-9-azabicyclo[3.3.1]non-7-yl]-1-(cyclopropylmethyl)indazole-3-carboxamide

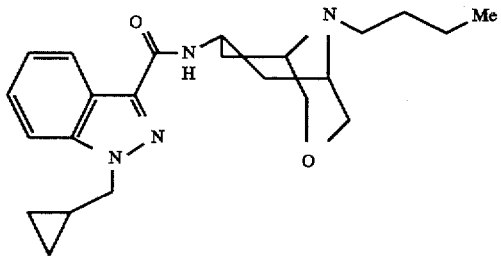

$^1$H NMR(CDCl$_3$) δ 0.43–0.47(m, 2H), 0.56–0.60(m, 2H), 0.94(t, J=7 Hz, 3H), 1.30–1.45(m, 4H), 1.50(d, J=15 Hz, 2H), 2.46(td, J=6 Hz, 15 Hz, 2H), 2.67(t, J=7 Hz, 2H), 2.74(bs, 2H), 3.86(d, J=11 Hz, 2H), 3.99(d, J=11 Hz, 2H), 4.28(d, J=7 Hz, 2H), 4.78(td, J=7 Hz, 11 Hz, 1H), 7.23–7.27 (m, 1H), 7.36–7.44(m, 2H), 8.39(d, J=8 Hz, 1H), 9.45(d, J=11 Hz, 1H)

The title compound was converted to the hydrochloride in accordance with the procedure described in Example 1.

m.p. 218°–220° C.

Example 14

N-[endo-9-(n-Pentyl)-3-oxa-9-azabicyclo[3.3.1]non-7-yl]-1-isopropylindazole-3-carboxamide

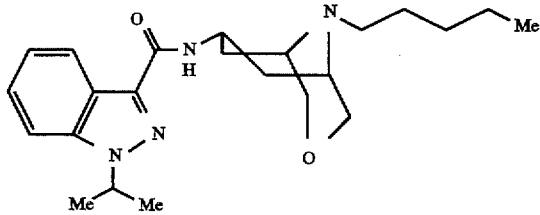

$^1$H NMR(CDCl$_3$) δ 0.92(t, J=7 Hz, 3H), 1.25–1.40(m, 4H), 1.41–1.46(m, 2H), 1.50(d, J=15 Hz, 2H), 1.60(d, J=7 Hz, 6H), 2.45(td, J=6 Hz, 215 Hz, 2H), 2.66(t, J=7 Hz, 2H), 2.73(bs, 2H), 3.85(d, J=11 Hz, 2H), 4.00(d, J=11 Hz, 2H), 4.77(td, J=6 Hz, 11 Hz, 1H), 4.85(sept, J=7 Hz, 1H), 7.22–7.26(m, 1H), 7.37(t, J=7 Hz, 1H), 7.44(d, J=8 Hz, 1H), 8.38(d., J=8 Hz, 1H), 9.50(d, J=11 Hz, 1H)

The title compound was converted to the hydrochloride in accordance with the procedure described in Example 1.

Example 15

N-[endo-9-(n-Pentyl)-3-oxa-9-azabicyclo[3.3.1]non-7-yl]-1-(3-pentyl)-indazole-3-carboxamide

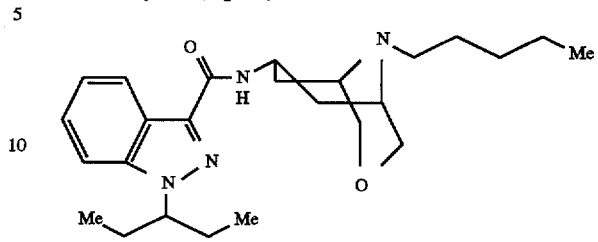

$^1$H NMR(CDCl$_3$) δ 0.75(t, J=7 Hz, 3H), 0.91(t, J=7 Hz, 3H), 1.25–1.35(m, 4H), 1.40–1.46(m, 2H), 1.50(d, J=15 Hz, 2H), 1.86–1.96(m, 2H), 2.05–2.16(m, 2H), 2.45(td, J=6 Hz, 15 Hz, 2H), 2.66(t, J=7 Hz, 2H), 2.73(bs, 2H), 3.82(d, J=11 Hz, 2H), 3.99(d, J=11 Hz, 2H), 4.26–4.33(m, 1H), 4.76(td, J=7 Hz, 11 Hz, 1H), 7.21–7.26(m, 1H), 7.35(dt, J=1 Hz, 8 Hz, 1H), 7.42(d, J=8 Hz, 1H), 8.38(d, J=8 Hz, 1H), 9.15(d, J=11 Hz, 1H)

The title compound was converted to the hydrochloride in accordance with the procedure described in Example 1.

Example 16

N-[endo-9-(n-Butyl)-3-oxa-9-azabicyclo[3.3.1]non-7-yl]-1-cyclopentyl-indazole-3-carboxamide

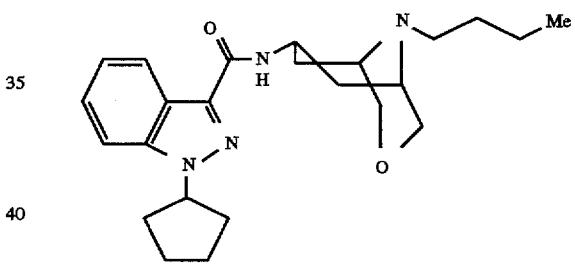

To a solution of N-[endo-9-(n-butyl)-3-oxa-9-azabicyclo [3.3.1]non-7-yl]-1H-indazole-3-carboxamide (1 g) in DMF (10 ml) were added triphenylphosphine (1.54 g) and cyclopentyl alcohol (0.72 g) and the mixture was stirred at room temperature. A solution of diethylazodicarboxylic acid (1.03 g) in DMF (4 ml) was added slowly thereto and the mixture was stirred for 15 hours. The reaction solution was concentrated under reduced pressure and the residue was purified by a silica gel column chromatography (ethyl acetate-hexane=2:1) to give the title compound (0.85 g).

$^1$H NMR(CDCl$_3$) δ0.94(t, J=7 Hz, 3H), 1.35–1.45(m, 4H), 1.48(d, J=15 Hz, 2H), 1.70–1.78(m, 2H), 1.95–2.04(m, 2H), 2.12–2.21(m, 2H), 2.45(td, J=6 Hz, 14 Hz, 2H), 2.67(t, J=7 Hz, 2H), 2.73(bs, 2H), 3.83(d, J=11 Hz, 2H), 3.99(d, J=11 Hz, 2H), 4.76(td, J=7 Hz, 11 Hz, 1H), 5.01(quint, J=7 Hz, 1H), 7.21–7.69 (m, 3H), 8.37(d, J=8 Hz, 1H), 9.56(d, J=11 Hz, 1H)

The title compound was converted to the hydrochloride in accordance with the procedure described in Example 1.

m.p. 208°–210° C.

The following compounds were prepared in a similar manner.

Example 17

N-[endo-9-(n-Butyl)-3-oxa-9-azabicyclo[3.3.1]non-7-yl]-1-(1-methyl-2-butynyl)indazole-3-carboxamide

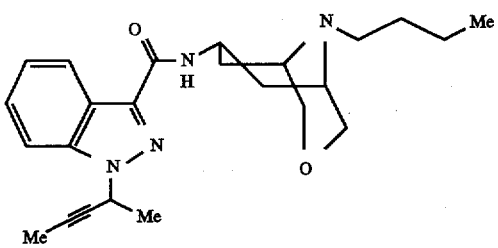

$^1$H NMR(CDCl$_3$) δ 0.94(t, J=7 Hz, 3 Hz), 1.27–1.46(m, 4H), 1.49(dd, J=8 Hz, 14 Hz, 2H), 1.83(d, J=10 Hz, 3H), 1.83(s, 3H), 2.45(td, J=7 Hz, 15 Hz, 2H), 2.66(t, J=7 Hz, 2H), 2.74(bs, 2H), 3.86(t, J=8 Hz, 2H), 3.99(d, J=11 Hz, 2H), 4.77(td, J=6 Hz, 10 Hz, 1H), 5.52–5.54(m, 1H), 7.25–7.28(m, 1H), 7.39(t, J=8 Hz, 1H), 7.71(d, J=8 Hz, 1H), 8.39(d, J=8 Hz, 1H), 9.42(d, J=11 Hz, 1H)

The title compound was converted to the hydrochloride in accordance with the procedure described in Example 1.
m.p. 210°–218° C.

Example 18

(S)-(+)-N-[endo-9-(n-Butyl)-3-oxa-9-azabicyclo[3.3.1]non-7-yl]-1-(sec-butyl)indazole-3-carboxamide The title compound was synthesized from N-[endo-9-(n-butyl)-3-oxa-9-azabicyclo[3.3.1]non-7-yl]-1H-indazole-3-carboxamide and (R)-(−)-sec-butyl alcohol in the same manner as in Example 16.

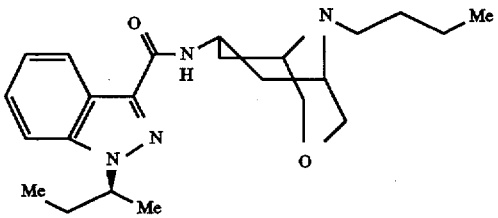

$^1$H NMR(CDCl$_3$) δ 0.80(t, J=7 Hz, 3H), 0.94(t, J=7 Hz, 3H), 1.34–1.44(m, 4H), 1.50(d, J=15 Hz, 2H), 1.58(d, J=7 Hz, 3H), 1.85–1.93(m, 1H), 2.07–2.14(m, 1H), 2.46(td, J=6 Hz, 15 Hz, 2H), 2.67(t, J=7 Hz, 2H), 2.74(bs, 2H), 3.83(d, J=11 Hz, 2H), 3.99(d, J=11 Hz, 2H), 4.54–4.60(m, 1H), 4.77(td, J=7 Hz, 11 Hz, 1H), 7.22–7.26(m, 1H), 7.36(t, J=7 Hz, 1H), 7.43(d, J=9 Hz, 1H), 8.38(d, J=8 Hz, 1H), 9.51(d, J=11 Hz, 1H) [α]$_D^{20}$=+18.12 (C: 1.007 in CHCl$_3$)

The title compound was converted to the hydrochloride in accordance with the procedure described in Example 1.
m.p. 198°–199° C.
[α]$_D^2$=+22.69 (C: 0.965 in CHCl$_3$)

Example 19

(R)-(−)-N-[endo-9-(n-Butyl)-3-oxa-9-azabicyclo[3.3.1]non-7-yl]-1-(sec-butyl)indazole-3-carboxamide The title compound was synthesized from N-[endo-9-(n-butyl)-3-oxa-9-azabicyclo[3.3.1]non-7-yl]-1H-indazole-3-carboxamide and (S)-(+)-sec-butyl alcohol in the same manner as in Example 16.

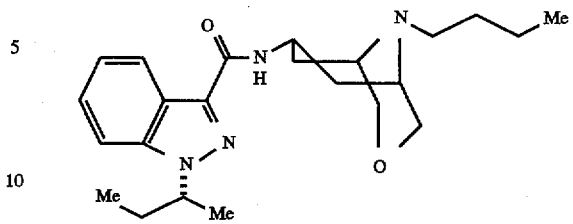

$^1$H NMR(CDCl$_3$) δ 0.80(t, J=7 Hz, 3H), 0.94(t, J=7 Hz, 3H), 1.33–1.45(m, 4H), 1.50(d, J=15 Hz, 2H), 1.58(d, J=7 Hz, 3H), 1.84–1.95(m, 1H), 2.07–2.14(m, 1H), 2.46(td, J=6 Hz, 15 Hz, 2H), 2.67(t, J=7 Hz, 2H), 2.74(bs, 2H), 3.84(d, J=11 Hz, 2H), 4.00(d, J=11 Hz, 2H), 4.53–4.62(m, 1H), 4.77(td, J=7 Hz, 11 Hz, 1H), 7.22–7.26(m, 1H), 7.36(dt, J=1 Hz, 7 Hz, 1H), 7.43(d, J=9 Hz, 1H), 8.38(dd, J=1 Hz, 8 Hz, 1H), 9.51(d, J=11 Hz, 1H)

[α]$_D^{20}$=−17.66 (C: 1.008 in CHCl$_3$)

The title compound was converted to the hydrochloride in accordance with the procedure described in Example 1.
m.p. 192°–194° C.
[α]$_D^{20}$=−20.99 (C: 0.362 in CHCl$_3$)

Comparative Example 1

N-[endo-9-Methyl-3-oxa-9-azabicyclo[3.3.1]non-7-yl]-1-methylindazole-3-carboxamide

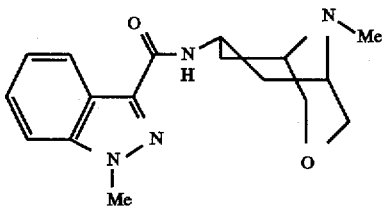

The title compound was synthesized in the same manner as mentioned in Example 4 of Japanese Patent Kokai 2-202890.

Comparative Example 2

N-[endo-9-Methyl-3-oxa-9-azabicyclo[3.3.1]non-7-yl]-1-isopropylindazole-3-carboxamide

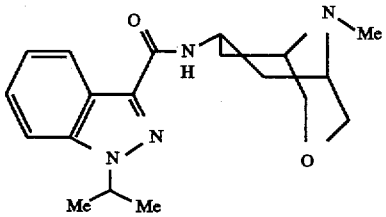

Reaction of endo-7-amino-9-methyl-3-oxa-9-azabicyclo[3.3.1]nonane with diindazolo[2,3-a][2',3+-d]-pyrazine-7,14-dione was carried out in the same manner as in Preparation Example 5 to form N-[endo-9-methyl-3-oxa-9-azabicyclo[3.3.1]non-7-yl]-1H-indazole-3-carboxamide, which was then treated in the same manner as in Example 1 to give the title compound.

¹H NMR(CDCl₃) δ 1.53(d, J=5 Hz, 2H), 1.60(d, J=7 Hz, 6H), 2.51–2.57(m, 2H), 2.57(s, 3H), 2.58(s, 2H), 3.85(d, J=11 Hz, 2H), 4.05(d, J=11 Hz, 2H), 4.78(td, J=7 Hz, 11 Hz, 1H), 4.82–4. 89(m, 1H), 7.22–7.24(m, 1H), 7.37(t, J=8 Hz, 1H), 7.45(d, J=8 Hz, 1H), 8.38(d, J=11 Hz, 1H), 9.48(d, J=11 Hz, 1H)

The title compound was converted to the hydrochloride in accordance with the procedure described in Example 1.

m.p. 220°–222° C.

Example 20

N-[endo-9-(n-Butyl)-3-oxa-9-azabicyclo[3.3.1]non-7-yl]-1H-5-benzyloxy-indazole-3-carboxamide

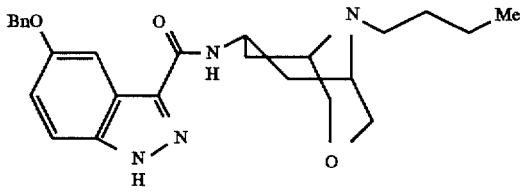

To a solution of endo-7-amino-9-(n-butyl)-3-oxa-9-azabicyclo[3.3.1]nonane (0.89 g) in DMF (30 ml) were added in turn 1H-5-benzyloxyindazole-3-carboxylic acid (0.80 g), diethylphosphorocyanidate (0.73 g) and triethylamine (0.63 ml) under ice-cooling and the mixture was stirred at room temperature for 13 hours. The reaction solution was poured into water and extracted with ethyl acetate. The organic layer was washed subsequently with a saturated aqueous solution of sodium hydrogencarbonate and saturated saline, dried over anhydrous sodium sulfate and concentrated under reduced pressure. The residue was dissolved in methanol, a 25% aqueous solution of sodium hydroxide was added and the resulting mixture was stirred at room temperature for 45 minutes and allowed to stand overnight. The reaction solution was concentrated and extracted with chloroform. The organic layer was washed with saturated saline and dried over anhydrous magnesium sulfate. The reaction solution was concentrated under reduced pressure and the residue was purified by a silica gel column chromatography (ethyl acetate) to give the title compound (0.93 g).

m.p. 275°–281° C.

¹H NMR(CDCl₃) δ 0.94(t, J=7 Hz, 3H), 1.35–1.44(m, 4H), 1.51(d, J=15 Hz, 2H), 2.46–2.51(m, 2H), 2.67(t, J=7 Hz, 2H), 2.76(bs, 2H), 3.87(d, J=11 Hz, 2H), 4.03(d, J=11 Hz, 2H), 4.76–4.82(m, 1H), 5.09(s, 2H), 7.14–7.16(m, 1H), 7.30–7.47(m, 6H), 7.91(d, J=2 Hz, 1H), 9.58(d, J=11 Hz, 1H), 10.85(bs, 1H)

Example 21

N-[endo-9-(n-Butyl)-3-oxa-9-azabicyclo[3.3.1]non-7-yl]-1H-7-benzyloxy-indazole-3-carboxamide

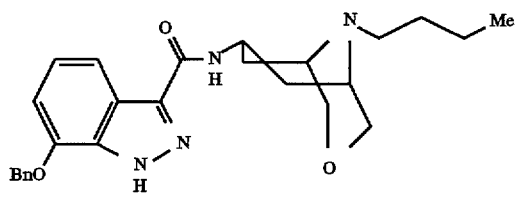

To a solution of endo-7-amino-9-(n-butyl)-3-oxa-9-azabicyclo[3.3.1]nonane (0.87 g) in DMF (30 ml) were added in turn 1H-7-benzyloxyindazole-3-carboxylic acid (0.87 g), diethylphosphorocyanidate (0.73 g) and triethylamine (0.63 ml) under ice-cooling and the mixture was stirred at room temperature for 13 hours. The reaction solution was poured into water and extracted with ethyl acetate. The organic layer was washed with saturated saline, dried over anhydrous sodium sulfate and concentrated under reduced pressure. The residue was purified by a silica gel column chromatography (ethyl acetate) to give the title compound (0.93 g) as pale yellow crystals.

m.p. 183°–185° C.

¹H NMR(CDCl₃) δ 6 0.93(t, J=7 Hz, 3H), 1.34–1.44(m, 4H), 1.49(d, J=15 Hz, 2H), 2.42–2.49(m, 2H), 2.66(t, J=7 Hz, 2H), 2.73(bs, 2H), 3.85(d, J=11 Hz, 2H), 4.00(d, J=11 Hz, 2H), 4.74–4.80(m, 1H), 5.23(s, 2H), 6.83(d, J=7 Hz, 1H), 7.14–7.18(m, 1H), 7.35–7.47(m, 5H), 7.97(d, J=8 Hz, 1H), 9.51(d, J=11 Hz, 1H), 10.41(bs, 1H)

Example 22

N-[endo-9-Benzyl-3-oxa-9-azabicyclo[3.3.1]non-7-yl]-1H-indazole-3-carboxamide

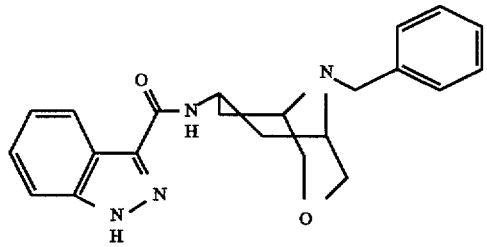

To a solution of endo-7-amino-9-benzyl-3-oxa-9-azabicyclo[3.3.1]nonane (1.00 g) in DMF(50 ml) were added in turn diindazolo[2,3-a][2',3'-d]pyrazine-7,14-dione (1.24 g), potassium carbonate(0.89 g) and dimethyl aminopyridine. (0.05 g) at room temperature and the mixture was stirred for 63 hours. To the reaction solution was added chloroform (200 ml) and the mixture was filtered with Celite. The filtrate was concentrated and the residue was purified by a silica gel column chromatography (ethyl acetate) to give the title compound as a yellowish brown solid. Recrystallization from ethyl acetate/isopropyl ether gave the title compound (0.42 g) as pale yellow crystals.

m.p. 296°–302° C. (dec.)

¹H NMR(CDCl₃) δ 1.55(d, J=15 Hz, 2H), 2.50–2.57(m, 2H), 2.74(bs, 2H), 3.88(d, J=11.7 Hz, 2H), 3.89(s, 2H), 4.07(d, J=11 Hz, 2H), 4.82–4.88(m, 1H), 7.24–7.51(m, 8H), 8.44(d, J=8 Hz, 1H), 9.61(d, J=11 Hz, 1H), 10.24(bs, 1H)

Example 23

N-[endo-9-(n-Butyl)-3-oxa-9-azabicyclo[3.3.1]non-7-yl]-5-benzyloxy-1-isopropylindazole-3-carboxamide

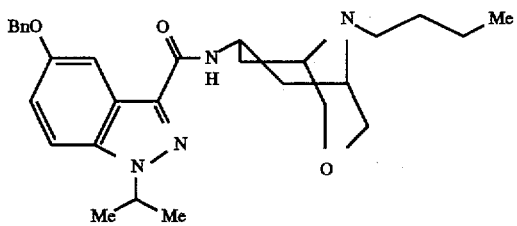

To a solution of N-[endo-9-(n-butyl)-3-oxa-9-azabicyclo[3.3.1]non-7-yl-]-1H-5-benzyloxyindazole-3-carboxamide (0.62 g) in DMF (20 ml) was added 60% sodium hydride (68 mg) at room temperature and the mixture was stirred for 45 minutes and then isopropyl bromide (0.21 g) was added. he resulting mixture was stirred at room temperature for a further 8 hours. The reaction solution was cooled with ice and the reaction was discontinued by the addition of saturated ammonim cloride (0.5 ml). The reaction mixture was poured into water and extracted with ethyl acetate. The organic layer was washed with saturated saline, dried over anhydrous sodium sulfate and concentrated under reduced pressure. The residue was purified by a silical gel column chromatography (chloroform:methanol:aqueous ammonia=50:1:05) to give the title compound (0.61 g).

m.p. 131°–133° C.

$^1$H NMR(CDCl$_3$) δ 0.94(t, J=7.3 Hz, 3H), 1.33–1.45(m, 4H), 1.50(d, J=15 Hz, 2H), 1.58(d, J=7 Hz, 6H), 2.43–2.50 (m, 2H), 2.67(t, J=7 Hz, 2H), 2.74(bs, 2H), 3.85(d, J=11 Hz, 2H), 4.00(d, J=11 Hz, 2H), 4.74–4.82(m, 1H), 4.81(sept, J=7 Hz, 1H), 5.14(s, 2H), 7.11–7.14(m, 1H), 7.31–7.41(m, 4H), 7.48(d, J=7 Hz, 2H), 7.89(d, J=2 Hz, 1H), 9.47(d, J=11 Hz, 1H)

Example 24

N-[endo-9-(n-Butyl)-3-oxa-9-azabicyclo[3.3.1]non-7-yl]-7-benzyloxy-1-isopropylindazole-3-carboxamide

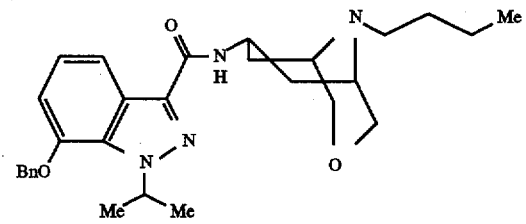

N-[endo-9-(n-Butyl)-3-oxa-9-azabicyclo[3.3.1]-non-7-yl]-1H-7-benzyloxyindazole-3-carboxamide (100 g) was subjected to isopropylation according to the same procedure as described in Example 23 and the product was recrystallized from isopropyl ether to give the title compound (0.46 g).

m.p. 151°–152° C.

$^1$H NMR(CDCl$_3$) δ 0.94(t, J=7 Hz, 3H), 1.34–1.45(m, 4H), 1.49(d, J=15 Hz, 2H), 1.53(d, J=6 Hz, 6H), 2.42–2.48 (m, 2H), 2.66(t, J=7 Hz, 2H), 2.73(bs, 2H), 3.83(d, J=11 Hz, 2H), 3.99(d, J=11 Hz, 2H), 4.75(td, J=7, 11 Hz, 1H), 5.22(s, 2H), 5.47(sept, J=7 Hz, 1H), 6.79(d, J=8 Hz, 2H), 7.11(t, J=8 Hz, 1H), 7.36–7.48(m, 5H), 7.96(d, J=8 Hz, 1H), 9.53(d, J=11 Hz, 1H)

Example 25

N-[endo-9-Benzyl-3-oxa-9-azabicyclo3.3.1]non-7yl]-1-isopropylindazole-3-carboxamide

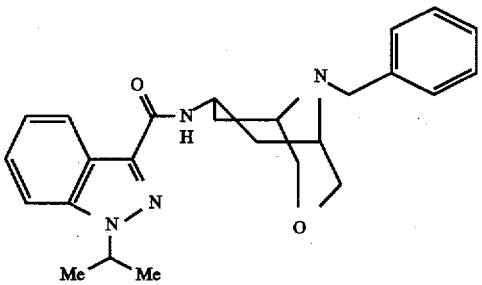

N-[endo-9-Benzyl-3-oxa-9-azabicyclo[3.3.]non-7-yl]-1H-indazole-3-carboxamide (0.42 g) was subjected to isopropylation according to the same procedure as described in Example 23 and the product was purified by a thin layer silica gel chromatography (chloroform:methanol:aqueous ammonia=20:1:0.5) to give the title compound (0.28 g) as pale yellow crystals.

m.p. 167°–169° C.

$^1$H NMR(CDCl$_3$) δ 1.54(d, J=15 Hz, 2H), 1.59(d, J=7 Hz, 6H), 2.48–2.55(m, 2H), 2.70(bs, 2H), 3.83(d, J=11 Hz, 2H), 3.88(s, 2H), 4.03(d, J=11 Hz, 2H), 4.81–4.88(m, 2H), 7.22–7.44(m, 8H), 8.39(d, J=8 Hz, 1H), 9.52(d, J=11 Hz, 1H)

Example 26

N-[endo-9-(n-Butyl)-3-oxa-9-azabicyclo[3.3.1]non-7-yl]-5-hydroxy-1-isopropylindazole-3-carboxamide (hydrochloride)

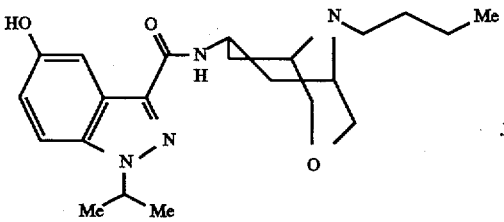

A solution of N-[endo-9-(n-butyl)-3-oxa-9-azabicyclo[3.3.1]non-7-yl]-5-benzyloxy-1-isopropylindazole-3-carboxamide (0.47 g) in methanol (30 ml) were added a 4N hydrogen chloride/ethyl acetate solution (0.5 ml) and 10% palladium on carbon (0.6 g) and the mixture was shaken under a hydrogen atmosphere until hydrogen absorption becomes slow. Then, the catalyst was filtered off with Celite and the filtrate was concentrated under reduced pressure. The residue was crystallized in ethyl acetate to give the title compound (0.25 g) as crystals.

m.p. 251°–269° C. (dec.)

$^1$H NMR(DMSO-d$_6$) δ 0.94(t, J=7 Hz, 3H), 1.34–1.40(m, 2H), 1.48(d, J=7 Hz, 6H), 1.72–1.76(m, 2H), 1.74(d, J=16 Hz, 2H), 2.63–2.67(m, 2H), 3.43(bs, 2H), 3.55(bs, 2H), 4.05(d, J=12 Hz, 2H), 4.47(d, J=12 Hz, 2H), 4.59–4.62(m, 1H), 4.94(sept, J=7 Hz, 1H), 6.97(d, J=9 Hz, 1H), 7.48(s, 1H), 7.58(d, J=9 Hz, 1H), 9.01(d, J=11 Hz, 1H)

Example 27

N-[endo-9-(n-Butyl)-3-oxa-9-azabicyclo[3.3.1]non-7-yl]-7-hydroxy-1-isopropylindazole-3-carboxamide (hydrochloride)

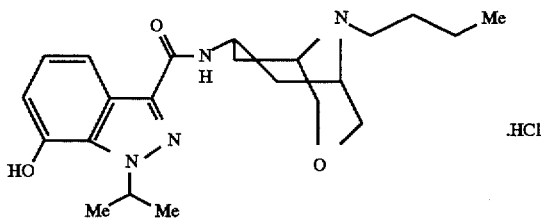

N-[endo-9-(n-Butyl)-3-oxa-9-azabicyclo[3.3.1]non-7-yl]-7-benzyloxy-1-isopropylindazole-3-carboxamide (0.41 g) was reduced according to the same procedure as described in Example 26 to give the title compound (0.33 g) as white crystals.

m.p. 270°–285° C. (dec.)
Free base
$^1$H NMR(CDCl$_3$) δ 0.93(t, J=7 Hz, 3H), 1.34–1.47(m, 4H), 1.50(d, J=15 Hz, 1H), 1.56(d, J=6 Hz, 6H), 1.64(bs, 1H), 2.42–2.49(m, 2H), 2.67(t, J=7 Hz, 2H), 2.75(bs, 2H), 3.84(d, J=11 Hz, 2H), 4.01(d, J=11 Hz, 2H), 4.75–4.78(m, 1H), 5.47–5.57(m, 1H), 6.68(d, J=7 Hz, 1H), 6.97–7.01(m, 1H), 7.88(d; J=8 Hz, 1H), 9.61(d, J=11 Hz, 1H)

Example 28

N-[endo-3-Oxa-9-azabicyclo[3.3.1]non-7-yl]-1-isopropylindazole-3-carboxamide (hydrochloride)

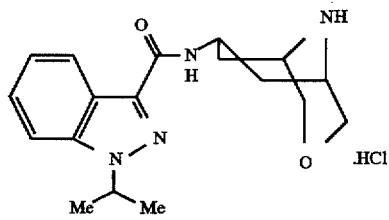

N-[endo-9-Benzyl-3-oxa-9-azabicyclo[3.3.1]non-7-yl]-1-isopropylindazole-3-carboxamide (0.26 g) was reduced according to the same procedure as described in Example 26 to give the title compound (0.14 g) as crystals.

m.p. 155°–163° (dec.)
$^1$H NMR(D$_2$O) δ 1.59(d, J=6 Hz, 6H), 2.20(d, J=16 Hz, 2H), 2.71–2.75(m, 2H), 3.81(bs, 2H), 4.19–4.28(m, 4H), 4.74–4.76(m, 1H), 5.01–5.08(m, 1H), 7.37–7.41(m, 1H), 7.53–7.57(m, 1H), 7.73(d, J=9 Hz, 1H), 8.14(d, J=8 Hz, 1H)

Example 29

The 5-HT$_4$ receptor agonistic activity of the present compounds was tested by the following method.

Ileum was excised from guinea pigs to prepare longitudinal muscle samples with approximately 2 cm length. The sample was suspended in Krebs-Henseleit liquid bath supplied with a mixed gas (95% O$_2$, 5% CO$_2$) and subjected to electrical stimulation (1 msec, 0.1 Hz) to record contraction force isometrically. The test compounds were dissolved in distilled water or DMSO and tested at a concentration of $10^{-7}$M (but $10^{-6}$M for Compound 11). The results are shown by the presence or absence of the increase in the contraction height by electrical stimulation before administration of the compound, wherein the symbol "+" indicates the increase in the contraction height, while "−" indicates no effect.

| Test compounds of the following examples | Ak | R | LMMP |
|---|---|---|---|
| Comparative Ex. 1 | Me | Me | − |
| Comparative Ex. 2 | Me | i-Pr | + |
| Example 2 | n-Pr | i-Pr | + |
| Example 5 | n-Bu | i-Pr | + |
| Example 8 | n-Bu | s-Bu | + |
| Example 11 | n-Bu | Allyl | + |
| Example 13 | n-Bu | Cyclopropylmethyl | + |
| Example 14 | n-Pentyl | i-Pr | + |

Whether or not the action of the above compounds is that via activation of 5-HT$_4$ receptors was investigated using as 5-HT$_4$ receptor antagonist, SDZ 205–557 (2-methoxy-4-amino-5-chlorobenzoic acid 2-(diethylamino)ethyl ester) described in Naunyn-Schmiedeberg's Arch Pharmacol (1992) 345:387–393. Thus, the investigation as to whether SDZ 205–557 can antagonize the increase in the contraction height of the above compounds using the longitudinal muscle preparation of the isolated guinea pig ileum can reveal that such increase in the contraction height is the action via activation of 5-HT$_4$ receptors.

It was verified that the increase in the contraction height of the above compounds was antagonized with $3\times10^{-7}$M SDZ 205–557 and this increase was the effect via 5-HT$_4$ receptors.

Example 30

The agonistic activity of oxazabicyclo derivatives and Mosapride on 5-HT$_4$ receptors was determined by the procedure mentioned in Naunyn-Schmiedeberg's Arch Pharmacol (1991) 343:439–446.

The rat oesophageal tunica muscularis mucosae were suspended in organ both containing Krebs-Henseleit solution aerated with a mixed gas (95% O$_2$, 5% CO$_2$) and contracted with carbachol ($1\times10^{-6}$M). After the contraction was stabilized, the cumulative administration of the compounds was performed to determine the relaxation of the rat oesophagus pre-contracted with carbachol. The concentration (ED$_{50}$) to cause 50% relaxation of the carbachol-induced contraction was measured. The result is expressed in terms of −log ED$_{50}$ and shown in the following table in which higher numerical value indicates higher activity.

| Compound of Example No. | Ak | R | Activity (-log ED$_{50}$) |
|---|---|---|---|
| Comparative Example 1 | Me | Me | 3.94 |
| Comparative Example 2 | Me | i-Pr | 5.82 |
| Example | | | |
| 2 | n-Pr | i-Pr | 5.54 |
| 3 | n-Pr | 3-Pentyl | 5.78 |

-continued

| Compound of Example No. | Ak | R | Activity (-log ED$_{50}$) |
|---|---|---|---|
| 4 | n-Bu | Et | 4.99 |
| 1 | n-Bu | n-Pr | 5.42 |
| 5 | n-Bu | i-Pr | 6.00 |
| 6 | n-Bu | n-Bu | 5.33 |
| 7 | n-Bu | i-Bu | 5.28 |
| 8 | n-Bu | sec-Bu | 6.20 |
| 18 | n-Bu | (S)-sec-Bu | 6.36 |
| 19 | n-Bu | (R)-sec-Bu | 5.98 |
| 9 | n-Bu | 2-Pentyl | 6.11 |
| 10 | n-Bu | 3-Pentyl | 6.07 |
| 11 | n-Bu | Allyl | 5.45 |
| 12 | n-Bu | 3-Me-2-butenyl | 5.17 |
| 17 | n-Bu | 1-Me-2-butynyl | 5.65 |
| 13 | n-Bu | Cyclopropylmethyl | 5.68 |
| 16 | n-Bu | Cyclopentyl | 5.11 |
| 14 | n-Pentyl | i-Pr | 5.83 |
| 15 | n-Pentyl | 3-Pentyl | 6.09 |
| 26(5-OH) | n-Bu | i-Pr | 4.98 |
| 27(7-OH) | n-Bu | i-Pr | 4.80 |
| 28 | H | i-Pr | 6.33 |
| Mosapride |  |  | 4.46 |

Example 31

For the purpose of studying a receptor selectivity of the present compounds, the 5-HT$_3$ receptor antagonist activity was tested in the following manner. Rats were anesthetized with urethane and heart rate was recorded through femoral artery. The 5-HT$_3$ selective agonist, 2-methyl-5-hydroxytryptamine (2-Me-5-HT) was administered at 0.1 mg/kg through carotid arteries and transient reduction in heart rate was recorded. The test. compounds were administered through jugular vein at 5 minutes before the administration of 2-Me-5-HT, inhibitory rate of reduction in heart rate by the administration of 2-Me-5-HT was calculated and IC$_{50}$ value was calculated from the inhibitory rate. The results are shown in the following table.

| Compound of Example No. | Ak | R | IC$_{50}$ (µg/kg, iv) |
|---|---|---|---|
| Comparative Example 2 | Me | i-Pr | 0.32 |
| Example |  |  |  |
| 2 | n-Pr | i-Pr | 8.9 |
| 5 | n-Bu | i-Pr | 42.7 |
| 14 | n-Pentyl | i-Pr | 28.1 |
| 8 | n-Bu | sec-Bu | 29.7 |
| 18 | n-Bu | (S)-sec-Bu | 18.3 |

The above results indicate that the 5-HT$_3$ receptor antagonistic activity of the present compounds is lower by at least 25 times than that of comparative Example 2 and thus the present compounds have higher selectivity for 5-HT$_4$ receptors.

Example 32

The present compounds were evaluated for the gastrointestinal prokinetic action, employing as an index the gastric-emptying promoting action. Fasted rats were orally given the test compound or distilled water. After 60 minutes, 3 ml of a test meal (a semi-solid food) was given into stomach by means of a probe. After 60 minutes, animals were sacrificed and stomach was excised and weighed. After washing out the gastric content, the stomach was again weighed to calculate the gastric content amount. The results were shown in the following table by calculating the gastric emptying rate (C) from the weight of the test meal given (A) and the weight of the test meal retained in the stomach (B), and expressing in terms of the gastric-emptying promoting rate to the gastric-emptying rate of the distilled water-given group(D).

Gastric-emptying rate(C)=(A−B)/A×100

Gastric-emptying promoting rate=C/D×100

| Test Compound | Dose (mg/kg) | Gastric-emptying promoting rate |
|---|---|---|
| Compound of Example 5 | 0.03 | 110.7 |
|  | 0.1 | 124.2 |
|  | 0.3 | 127.5 |
| Mosapride | 0.3 | 103.5 |
|  | 1 | 125.3 |
|  | 3 | 128.1 |

Example 33

The present compounds were investigated for the gastrointestinal motility activity by the following procedure, by which the gastrointestinal prokinetic action was confirmed.

Beagle dogs inserted with a forced transducer at the anterior wall of stomach were used after a convelescence period of more than one month.

Dogs fasted overnight were given a food (375 g of a dog food) and gastric motility after meal was determined. After 60 minutes of the feeding, the test compounds were intravenously injected and the promoting action on gastric motility after meal was determined. The area under contracting wave forms of gastric motility (Motility Index: MI) was calculated and expressed in terms of percentage to the MI at 15 minutes before the administration of the test compound.

| Test Compound | Dose (mg/kg) | MI (%) |
|---|---|---|
| Compound of Example 5 | 0.03 | 145.8 |
|  | 0.1 | 208.2 |
|  | 0.3 | 324.9 |
| Mosapride | 1 | 151.0 |

Example 34

Safety of the present compounds was investigated by the following method.

The compound of Example 5 was repeatedly administered orally to rats (male, female) over the period of 2 weeks to perform a toxicological investigation. As a result, no toxicological changes were observed at a dose of mg/kg. In addition, the compound of Example 5 showed negative in all tests of reverse mutation test (Ames test), chromosomal aberration test and micronucleus test, and no mutagenicity was observed.

The following examples illustrate pharmaceutical formulations.

| Tablets (per tablet) | |
|---|---|
| Compound of Example 5 (malonate) (Active ingredient) | 10 mg |
| Lactose | 64 mg |
| Crystalline cellulose | 15 mg |
| Corn starch | 7 mg |
| Hydroxypropylcellulose | 3 mg |
| Magnesium stearate | 1 mg |

The above ingredients were uniformly blended to prepare powders for direct compression. The powders were formed in a rotary tableting machine to tablets each 6 mm in diameter and weighing 100 mg.

| Sugar-coated tablets (per tablet) | |
|---|---|
| Compound of Example 5 (malonate) (Active ingredient) | 10 mg |
| Lactose | 64 mg |
| Crystalline cellulose | 15 mg |
| Corn starch | 7 mg |
| Hydroxypropylcellulose | 3 mg |
| Magnesium stearate (coating agent) | 1 mg |
| Saccharose | 92 mg |
| Gum arabic | 3.2 mg |
| Gelatin | 0.7 mg |
| Precipitated calcium carbonate | 20 mg |

The above ingredients were uniformly blended to prepare powders for direct compression. The powders were formed in a rotary tableting machine to tablets each 6 mm in diameter and weighing 100 mg. The tablets are coated with the coating agents of the above composition according to a conventional method to prepare the sugar-coated tablets.

| Hard capsules (per capsule) | |
|---|---|
| Compound of Example 5 (malonate) (Active ingredient) | 10 mg |
| Lactose | 64 mg |
| Crystalline cellulose | 15 mg |
| Corn starch | 7 mg |
| Hydroxypropylcellulose | 3 mg |
| Magnesium stearate | 1 mg |

The above ingredients were uniformly blended, pressed and pulverized to prepare granules. The granules are filled in a capsule to prepare a hard-capsule.

| Granules (per divided packet) | |
|---|---|
| Compound of Example 5 (malonate) (Active ingredient) | 10 mg |
| Lactose | 90 mg |
| Corn starch | 50 mg |
| Crystalline cellulose | 50 mg |
| Hydroxypropylcellulose | 10 mg |
| Ethanol | 9 mg |

The active ingredient, lactose, corn starch and crystalline cellulose were uniformly blended and a solution of hydroxypropylcellulose in ethanol was added. The mixture was kneaded and granulated by an extrusion granulation method. The granules were then dried in a drier at 50° C. The dried granules were screened to granule sizes between 297 μm and 1460 μm to give a granule formulation weighing 200 mg per divided packet.

| Syrups | |
|---|---|
| Compound of Example 5 (malonate) (Active ingredient) | 1.000 g |
| Refined sugar | 30.000 g |
| D-sorbitol, 70 w/v% | 25.000 g |
| Ethyl paraoxybenzoate | 0.030 g |
| Propyl paraoxybenzoate | 0.015 g |
| Flavor | 0.200 g |
| Glycerin | 0.150 g |
| 96% Ethanol | 0.500 g |
| Distilled water | q.s. |

The active ingredient, refined sugar, D-sorbitol, ethyl paraoxybenzoate and propyl paraoxybenzoate were dissolved in 60 g of warm water. After cooling, glycerin and a solution of the folavor in ethanol were added. Distilled water was added to the mixture to make up a total amount of 100 ml.

| Injections | |
|---|---|
| Compound of Example 5 (malonate) (Active ingredient) | 1 mg |
| Sodium chloride | 10 mg |
| Distilled water | q.s. |

The active ingredient and sodium chloride were dissolved in distilled water to make up a total amount of 1.0 ml.

| Suppositories per piece | |
|---|---|
| Compound of Example 5 (malonate) (Active ingredient) | 2 g |
| Polyethylene glycol 4000 | 20 g |
| Glycerin | 78 g |

The active ingredient was dissolved in glycerin. To the solution was added polyethylene glycol 4000 and the mixture was warmed to a solution. The solution was poured into a suppository mold and solidified by cooling to prepare suppositories weighing 1.5 g per piece.

What is claimed is:

1. A compound of formula (I) or a pharmaceutically acceptable salt thereof:

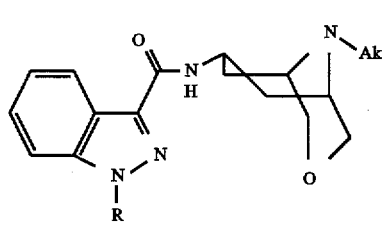

(I)

wherein Ak is a $C_3$–$C_6$ alkyl group, and R is a $C_3$–$C_6$ alkyl group, a $C_3$–$C_6$ alkenyl group, a $C_3$–$C_6$ alkynyl group, a $C_3$–$C_7$ cycloalkyl group or a $C_3$–$C_6$ cycloalkylmethyl group.

2. The compound of claim 1 wherein Ak is n-propyl, n-butyl or n-pentyl group and R is a $C_3$–$C_5$ alkyl group, a $C_3$–$C_5$ alkenyl group, 1-methyl-2-butynyl, cyclopentyl or cyclopropylmethyl group.

3. The compound of claim 1 which is N-[endo-9-(n-butyl)-3-oxa-9-azabicyclo[3.3.]non-7-yl]-1-isopropylindazole-3-carboxamide.

4. The compound of claim 1 which is N-[endo-9-(n-butyl)-3-oxa-9-azabicyclo[3.3.]non-7-yl]-1-(sec-butyl)indazole-3-carboxamide.

5. The compound of claim 1 which is (S)-(+)-N-[endo-9-(n-butyl)-3-oxa-9-azabicyclo[3.3.1]non-7-yl]-1-(sec-butyl)indazole-3-carboxamide.

6. A 5-$HT_4$ receptor agonist which comprises as an active ingredient a compound of claim 1 or a pharmaceutically acceptable salt thereof.

7. The 5-$HT_4$ receptor agonist of claim 6 for use in the treatment of digestive tract diseases.

8. The 5-$HT_4$ receptor agonist of claim 6 for use as a gastrointestinal prokinetic agent.

9. A pharmaceutical composition comprising as an active ingredient a compound of claim 1 or a pharmaceutically acceptable salt thereof and a pharmaceutically acceptable carrier.

10. A pharmaceutical composition of claim 9 for use in the treatment of digestive tract diseases.

11. The compound of claim 1, wherein Ak is a $C_4$–$C_6$ alkyl group.

* * * * *

UNITED STATES PATENT AND TRADEMARK OFFICE
CERTIFICATE OF CORRECTION

PATENT NO. : 5,684,003
DATED : November 4, 1997
INVENTOR(S) : Haruhiko Kikuchi, et. al.

It is certified that error appears in the above-identified patent and that said Letters Patent is hereby corrected as shown below:

Column 41, lines 3, 4 and 5, "N-[endo-9-(n-butyl)-3-oxa-9-azabicyclo[3.3.]non-7-yl]-1-isopropylindazole-3-carboxamide" should read --N-[endo-9-(n-butyl)-3-oxa-9-azabicyclo[3.3.1]non-7-yl]-1-isopropylindazole-3-carboxamide--;

lines 6, 7 and 8, "N-[endo-9-(n-butyl)-3-oxa-9-azabicyclo[3.3.]non-7-yl]-1-(sec-butyl)indazole-3-carboxamide" should read --N-[endo-9-(n-butyl)-3-oxa-9-azabicyclo[3.3.1]non-7-yl]-1-(sec-butyl)indazole-3-carboxamide--.

Signed and Sealed this

Tenth Day of March, 1998

BRUCE LEHMAN

Attest:

Attesting Officer

Commissioner of Patents and Trademarks